(12) United States Patent
Labib et al.

(10) Patent No.: US 11,033,624 B2
(45) Date of Patent: Jun. 15, 2021

(54) MEDICAL ITEM FOR PREVENTION AND TREATMENT OF EAR INFECTION

(71) Applicant: Novaflux Inc., Princeton, NJ (US)

(72) Inventors: Mohamed Emam Labib, Princeton, NJ (US); Stanislav S. Dukhin, Golden Bridge, NY (US)

(73) Assignee: Novaflux Inc., Princeton, NJ (US)

( * ) Notice: Subject to any disclaimer, the term of this patent is extended or adjusted under 35 U.S.C. 154(b) by 0 days.

(21) Appl. No.: 14/296,608

(22) Filed: Jun. 5, 2014

(65) Prior Publication Data

US 2015/0352260 A1   Dec. 10, 2015
US 2016/0121029 A9   May 5, 2016

Related U.S. Application Data

(63) Continuation-in-part of application No. 12/802,207, filed on Jun. 2, 2010, now Pat. No. 8,747,883.

(51) Int. Cl.

| | | |
|---|---|---|
| A61K 31/496 | (2006.01) | |
| A61L 31/04 | (2006.01) | |
| A61K 31/16 | (2006.01) | |
| A61K 45/06 | (2006.01) | |
| A61K 31/573 | (2006.01) | |
| A61K 31/765 | (2006.01) | |
| A61L 31/16 | (2006.01) | |

(52) U.S. Cl.
CPC ............ *A61K 45/06* (2013.01); *A61K 31/496* (2013.01); *A61K 31/573* (2013.01); *A61K 31/765* (2013.01); *A61L 31/041* (2013.01); *A61L 31/16* (2013.01); *A61L 2300/406* (2013.01); *A61L 2300/41* (2013.01); *A61L 2430/14* (2013.01)

(58) Field of Classification Search
None
See application file for complete search history.

(56) References Cited

U.S. PATENT DOCUMENTS

| | | | |
|---|---|---|---|
| 4,405,306 A | 9/1983 | Cadarelli | |
| 4,863,444 A | 9/1989 | Blomer | |
| 5,026,378 A | 6/1991 | Goldsmith, III | |
| 5,302,397 A | 4/1994 | Amsden et al. | |
| 5,350,580 A | 9/1994 | Muchow et al. | |
| 5,489,286 A | 2/1996 | Cinberg et al. | |
| 5,512,055 A * | 4/1996 | Domb .................. | A61K 9/0024 128/207.14 |
| 5,601,835 A | 2/1997 | Sabel et al. | |
| 5,633,000 A * | 5/1997 | Grossman ............ | A61K 31/485 424/422 |
| 6,120,484 A | 9/2000 | Silverstein | |
| 6,361,526 B1 | 3/2002 | Reisdorf et al. | |
| 6,379,323 B1 | 4/2002 | Patterson | |
| 6,589,286 B1 | 7/2003 | Littler | |
| 6,641,831 B1 | 11/2003 | Schierholz | |
| 6,676,930 B2 | 1/2004 | Mautone | |
| 6,723,333 B1 * | 4/2004 | Albers ..................... | A61L 29/16 424/422 |
| 8,187,254 B2 | 5/2012 | Hissink et al. | |
| 8,318,817 B2 * | 11/2012 | Lichter ................ | A61K 9/0024 424/486 |
| 8,366,660 B2 | 2/2013 | Wang | |
| 8,747,883 B2 | 6/2014 | Labib et al. | |
| 9,326,943 B1 | 5/2016 | Skovlund | |
| 2004/0024018 A1 * | 2/2004 | Kanikanti ............ | A61K 9/2054 514/312 |
| 2006/0018948 A1 | 1/2006 | Guire et al. | |
| 2007/0254035 A1 | 11/2007 | Hao et al. | |
| 2008/0318918 A1 | 12/2008 | Campbell et al. | |
| 2009/0076480 A1 | 3/2009 | Pudleiner et al. | |
| 2009/0138074 A1 | 5/2009 | Freyman | |
| 2009/0171464 A1 | 7/2009 | Imhof | |
| 2009/0171465 A1 | 7/2009 | Bucay-Couto et al. | |
| 2009/0263460 A1 | 10/2009 | McDonald | |
| 2009/0311304 A1 | 12/2009 | Borck et al. | |
| 2010/0121285 A1 | 5/2010 | Illi et al. | |
| 2010/0174366 A1 * | 7/2010 | Avior ..................... | A61F 11/002 623/10 |
| 2010/0273864 A1 | 10/2010 | Lichter et al. | |
| 2011/0300202 A1 * | 12/2011 | Labib .................. | A61K 9/0024 424/423 |
| 2012/0165795 A1 | 6/2012 | Seiler | |
| 2013/0129807 A1 | 5/2013 | Devore | |
| 2014/0107423 A1 | 4/2014 | Yaacobi | |
| 2015/0351967 A1 | 12/2015 | Lim et al. | |
| 2015/0352260 A1 | 12/2015 | Labib et al. | |
| 2016/0022497 A1 | 1/2016 | Labib et al. | |

FOREIGN PATENT DOCUMENTS

| | | | |
|---|---|---|---|
| WO | WO 2007/149771 A2 | 12/2007 | |
| WO | WO 2009/001358 A2 | 12/2008 | |
| WO | WO 2009/035562 A2 | 3/2009 | |
| WO | WO 2009/051819 A1 | 4/2009 | |
| WO | WO 2009051819 A1 * | 4/2009 | ........... A61K 9/0024 |
| WO | WO 2009/129439 | 10/2009 | |
| WO | WO2011152857 | 12/2011 | |
| WO | WO2012128720 | 9/2012 | |
| WO | WO2014051524 | 4/2014 | |

OTHER PUBLICATIONS

Labib et al. Colloids and Surfaces A: Physicohcemical and Engineernig Aspects 354, p. 331-337, 2010.*
Roland, Peter S., et al. "Topical ciprofloxacin/dexamethasone is superior to ciprofloxacin alone in pediatric patients with acute otitis media and otorrhea through tympanostomy tubes." The Laryngoscope 113.12 (2003): 2116-2122.*
Merkus, Henk G. "Particle size, size distributions and shape." Particle Size Measurements (2009): 13-42. APA.*
DuPont™ Elvax® EVA resins for Adhesives, Sealants and Wax Blends. © 2012.*
Defintion of "solid solution" from dictionary.com, accessed Oct. 31, 2017.*

(Continued)

*Primary Examiner* — Nissa M Westerberg
(74) *Attorney, Agent, or Firm* — Merchant & Gould P.C.

(57) ABSTRACT

Methods of preventing and treating an ear infection comprising insertion of a tympanostomy tube comprised of a least one anti-biotic agent.

16 Claims, 18 Drawing Sheets

(56) References Cited

OTHER PUBLICATIONS

Crowley, Michael M., et al. "Pharmaceutical applications of hot-melt extrusion: part I." Drug development and industrial pharmacy 33.9 (2007): 909-926. (Year: 2007).*
Van Laarhoven, J. A. H., M. A. B. Kruft, and H. Vromans. "Effect of supersaturation and crystallization phenomena on the release properties of a controlled release device based on EVA copolymer." Journal of Controlled release 82.2-3 (2002): 309-317. (Year: 2002).*
Eu, Byung Chan. "Irreversible thermodynamic theory of shear-induced melting point depression." Physica A: Statistical Mechanics and its Applications 160.1 (1989): 87-97 (Year: 1989).*
Peter D. Eimas, et al.; Otitis Media, Hearing Loss, and Child Development: a NICHD Conference Summary; Public Health Reports May-Jun. 1986, vol. 101, No. 3 pp. 289-293.
Lauren Bakaletz; Otitis Media—Polymicrobial Diseases—NCBI Bookshelf Chap. 14 Otitis Media; 2002, ASM Press; https://www.ncbi.nlm.nih.gov/books/NBK2482/?report=printable.
Ramsey Alsarraf, et al.; Measuring the Indirect and Direct Costs of Acute Otitis Media; Arch. Otolaryngol. Head Neck Surg vol. 125, Jan. 1999 pp. 12-18.
Aaron T. Curns, et al.; Outpatient and Hospital Visits Associated With Otitis Media Among American Indian and Alaska Native . . . Pediatrics vol. 109 No. 3 Mar. 2002, pp. 1-6.
Ellen R, Wald, et al.; Frequency and severity of infections in day care; The Journal of Pediatrics, vol. 112, No. 4, pp. 540-546. Apr. 1988.
David W. Teele, et al.;Otitis Media in Infancy and Intellectual Ability, School Achievement, Speech, and Language at Age . . . The Journal of Infectious Diseases 1990;162:685-694.
Richard M. Rosenfeld et al.; Clinical practice guideline: Otitis media with effusion; Otolaryngology—Head and Neck Surgery, vol. 130, No. 5, May 2004.
Collette Ah-Tye, et al.; Otorrhea in Young Children After Tympanostomy-Tube Placement for Persistent Middle-Ear . . . Pediatrics, vol. 107, No. 6, pp. 1251-1258 Jun. 2001.
Mohamed E. Labib, et al.; The long-term release of antibiotics from monolithic nonporous polymer . . . Colloids and Surfaces A: Physicochem. Eng. Aspects 354 (2010) 331-337.
Stanislav S. Dukhin, et al.; Theory of effective drug release from medical implants based on the Higuchl . . . Colloids and Surfaces A: Physicochem. Eng. Aspects 409 (2012) 10-20.
Minori Matsumoto et al.; Mutations in the gyrA and parC genes and in vitro activities of fluoroquinolones . . . International Journal of Antimicrobial Agents 40 (2012) 440-444.
S. M. Tambe, et al.; In vitro evaluation of the risk of developing bacterial resistance to antiseptics and antibiotics.Journal of Antimicrobial Chemotherapy (2001)47, 589-598.
Paul Stoodley, et al.; Characterization of a mixed MRSA/MRSE biofilm in an explanted total ankle arthroplasty; FEMS Immunol Med Microbiol 62 (2011) 66-74.
Ellen M. Mandel, et al.; Acute otorrhea: Bacteriology of a common complication of tympanostomy tubes; Ann Otol Rhino! Laryngol 103: 1994 (pp. 713-718).
Farrel J Buchinsky, et al.; Virulence phenotypes of low-passage clinical isolates of Nontypeable . . . BMC Microbiology 2007, 7:56 http://www.biomedcentral.com/1471-2180/7/56.
Wynn Kapit et al.; The Anatomy Coloring Book, Third Edition; p. 99; 1994.
Rodney M. Donlan, et al.; Biofilms: Survival mechanisms of clinically relevant mircoorganisms; Clinical Microbiology Reviews, Apr. 2002, vol. 15, No. p. 167-193.
John Newman; Mass transfer to the rear of a cylinder at high Schmidt numbers; I&EC Fundamentals vol. 8 No. 3 ; pp. 553-557; Aug. 1969.
Daniel Bonn, et al.; Wetting and Spreading; Reviews of modern physics, vol. 81, Apr.-Jun. 2009, pp. 739-805.
Jens Eggers; Hydrodynamic Theory of Forced Dewetting; Physical Review Letters, vol. 93, No. 9, 2004.
Jens Eggers; Existence of receding and advancing contact lines; Physics of Fluids 17, 082106 2005.
Y.I. Frenkel; On the behavior of liquid drops on a solid surface 1. The sliding of drops on an inclined surface; J. Exptl. Theoret. Phys. (USSR), 18, 659, 1948.
Shinichi Sano, et al.; Micropathologic Changes of Pars Tensa in Children With Otitis Media With Effusion; Arch Otolaryngol Head Neck Surg. 1994;120:815-819.
Ellen M. Mandel et al.; Myringotomy With and Without Tympanostomy Tubes for Chronic Otitis Media With Effusion; Arch Otolaryngol Head Neck Surg. 1989;115:1217-1224.
David J. Arnold, et al.; Permeability of tympanotomy tubes to ototopical preparations; Otolaryngology—Head and Neck Surgery, Jul. 1999, pp. 35-37.
Richard M. Rosenfeld; Surgical prevention of otitis media; Vaccine 19 (2001) S134-S139.
Elizabeth R. Ramos, et al.; Clinical effectiveness and risk of emerging resistance associated with prolonged use of . . . ;Crit Care Med 2011 vol. 39, No. 2, pp. 245-251.
Otavio B. Piltcher, et al.; A rat model of otitis media with effusion caused by eustachian tube obstruct . . . ;Otolaryngology—Head and Neck Surgery, vol. 126 No. 5, pp. 490-498.
Patricia A. Hebda, et al.; Cytokine Profiles in a Rat Model of Otitis Media With Effusion Caused by Eustachian Tube . . . ; Laryngoscope 112: Sep. 2002, pp. 1657-1662.
Rodrigo C. Silva, et al.; Novel rat model of tympanostomy tube otorrhea; International Journal of Pediatric Otorhinolaryngology 76 (2012) 179-182.
Phillip H. Gallo, et al.; Demonstration of Bacillus cereus in Orthopaedic-Implant-Related Infection with Use of a Multi-Primer . . . ; J Bone Joint Surg Am. 2011;93:e85(1-6).
Patricia A. Hebda, et al.; Effects of Ciprofloxacin-Dexamethasone on Myringotomy Wound Healing; Laryngoscope 117: Mar. 2007, pp. 552-528.
Sharon Freeman, et al.; Objective Method for Differentiating Between Drug-Induced Vestibulotoxicity and Cochleotoxicity; Otology & Neurotology, vol. 22, No. 1, 2001, pp. 70-75.
Michael L. Forbes, et al.; Strain-Specific Virulence Phenotypes of *Streptococcus pneumoniae* Assessed Using the Chinchilla . . . ; PLoS ONE, Apr. 2008, vol. 3, Is. 4, e1969, p1-11.
Roland, Peter S., et al. "Topical ciprofloxacin/dexamethasone is superior to ciprofloxacin alone in pediatric patients with acute otitis media and otorrhea through tympanostomy tubes." The Laryngoscope 113.12 (2009); 2116-2122.
Merlcus, Henk Gl. "Particle size, size distributions and shape." Particle Size Measurements (2009): 13-42. APA.
DuPont™ Elvax® EVA resins for Adhesives, Sealants and Wax Bends. © 2012.
Lee et al., "Overview of Controlled-Release Drug Delivery," p.1-13 in "Controlled-Release Technology," ACS Symposium Series 348 Amer. Chem. Society Washington DC 1987.
Scheirholz et al., "Controlled Release of Antibiotics From Biomedical Polyurethanes: Morphological and Structural Features," Biomaterials, 18 (12), 839-844 (1997).
Sprocket et al., "A Melt Extrusion Process for Manufacturing Matrix Drug Delivery Systems," Int. J. of Pharmaceutics, vol. 155, pp. 191-199 (1997).

\* cited by examiner

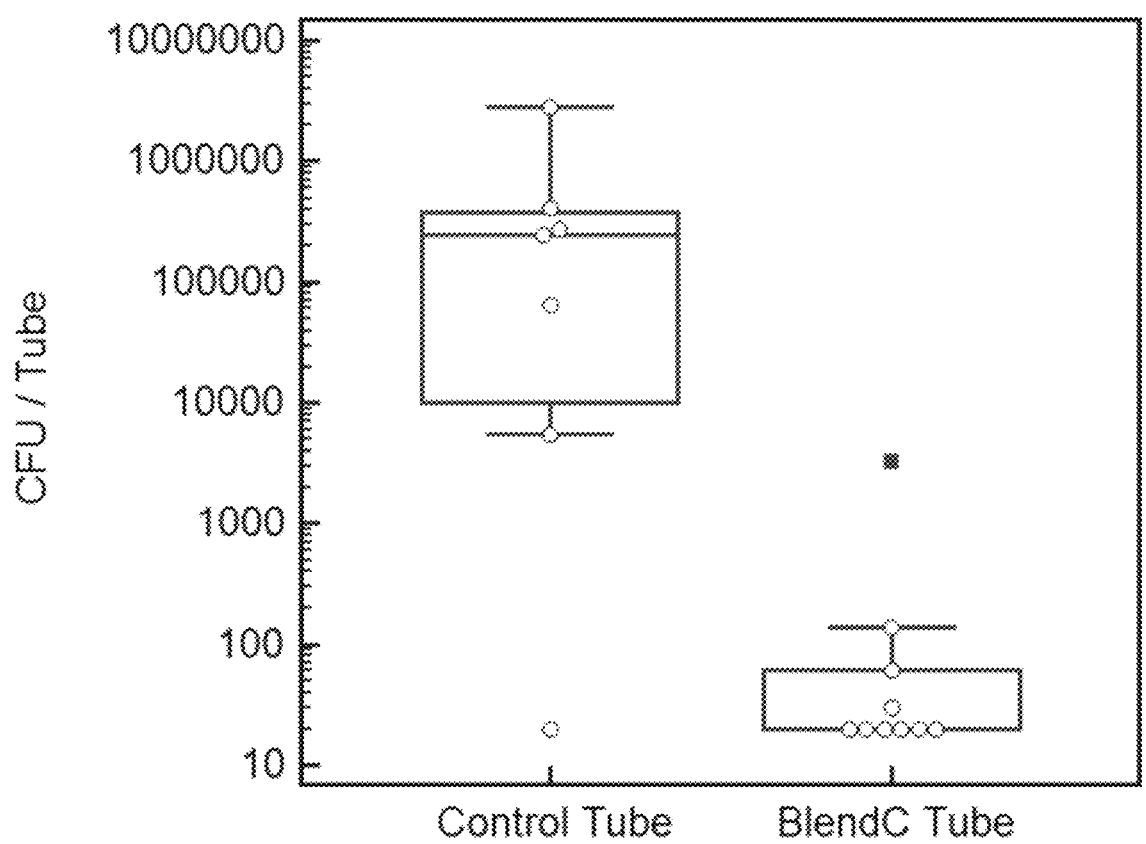

MEDICAL ITEM FOR PREVENTION AND TREATMENT OF EAR INFECTION

CROSS REFERENCE TO RELATED APPLICATIONS

This application is a continuation-in-part of application Ser. No. 12/802,207 filed Jun. 2, 2010 and published as US 2011/0300201 on Dec. 8, 2011. The disclosures of application Ser. No. 12/802,207 are hereby incorporated herein by reference to the extent not incompatible herewith.

BACKGROUND OF THE INVENTION

1. Field of the Invention

The invention relates to polymeric articles capable of releasing drugs at therapeutic levels over extended periods of time and to methods to prevent or treat infection.

2. Description of the Related Art

An ideal drug delivery system has been suggested to be one which provides the drug only when and where it is needed, and in the minimum dosage required to elicit the desired therapeutic effects. Extended release technology permits delivery to a patient of drug concentrations at therapeutic levels for extended periods without the need for repeated dosage and consequent cycling concentrations.

A great many specific systems for controlled release of drugs from polymers have previously been described. These systems may be broadly classified as follows:
  Bioerodible systems. e.g., WO 2009/129439 A2
  Drug-polymer chemical conjugates
  Membrane-reservoir systems
  Osmotic pumping
  Osmotic rupturing. e.g., U.S. Pat. No. 5,302,397
  Porous polymers
  Polymer erosion
  Polymer swelling
  Diffusion through a matrix This latter approach of diffusion through a matrix has been extensively employed for example in U.S. Pat. Nos. 4,863,444; 6,361,526 B1; 6,641,831 B1; 6,723,333 B1; United States Patent Applications 2009/0076480 A1; 2009/0171465; and in publications such as:
Sprockel et al, "A Melt Extrusion Process For Manufacturing Matrix Drug Delivery Systems", *Int. J. Pharmaceutics,* 155, 191-199 (1997)
Schierholz et al., "Controlled Release of Antibiotics From Biomedical Polyurethanes: Morphological and Structural Features". *Biomaterials,* 18, No. 12, 839-844 (1997)
P. I Lee and W. R. Good, Eds., "Overview of Controlled-Release Drug Delivery" in "Controlled Release Technology", ACS Symposium Series 348, American Chemical Society, Washington, D., 1987

Drug delivery by diffusion through a matrix has been described and criticized as follows:

"Historically, the most popular diffusion-controlled delivery system has been the matrix system, such as tablet and granules, where the drug is uniformly dissolved or dispersed, because of its low cost and ease of fabrication. However, the Inherent drawback of the matrix system is its first-order release behavior with continuously diminishing release rate." (emphasized in original)

P. I Lee and W. R. Good, Eds., "Controlled Release Technology", American Chemical Society, Washington, D., P. 5, 1987

The articles of the invention are solid, non-porous composites prepared by uniformly dispersing a bioactive agent in a non-biodegradable thermoplastic polymer melt, then cooling to a non-porous solid state. The composites can be made at a high drug volume fraction and under conditions that do not degrade the drug substance or produce toxic byproducts. The composite may be formed into useful articles by methods of plastics processing such as extrusion, compression, or injection molding. The drug is released by diffusion through the polymer matrix over a prolonged period of time without erosion, dissolution or disintegration. The inventive articles have the merits of low cost and ease of fabrication combined with extended drug release and essentially constant drug release rate after an initial induction period. Examples of the inventive articles containing antibiotics have long-term antibacterial effect without cytotoxicity to fibroblasts, and without irritation or inflammations of tissue. This surprising combination of properties satisfies long standing, but unmet needs.

SUMMARY OF THE INVENTION

In a first embodiment, the invention is a method of preventing an ear infection. said method comprising insertion of a tympanostomy tube in an ear drum by myrangotomy, said tympanostomy tube being comprised of a solid, non-porous composite comprised of:
  a) a melt blend of:
    (i) an ethylene-vinyl acetate copolymer having a melt index less than about 50 g/10 min. as measured by ASTM D1238 and comprising 10 to 50 percent by weight of vinyl acetate,
    (ii) polyethylene glycol having a weight average molecular weight of from about 2,000 to about 20000 Daltons; and
  b) one or more bioactive agents comprising at least ciprofloxacin antibiotic dispersed uniformly throughout said polymer material; said bioactive agents comprising about 1 to about 60 percent by weight of said polymer plus bioactive agents;
    wherein said ciprofloxacin is present in said polymer material as:
      i) a solid solution phase with said polymer material comprised of from about 0.1 to about 30 percent by weight of said ciprofloxacin; and
      ii) a solid solution phase with said polymer material comprised of from about 95 to about 99.99 percent by weight of said ciprofloxacin; and
      iii) a phase selected from a supersaturated solution, essentially pure ciprofloxacin, a solid solution comprised of ciprofloxacin and their combination.

In a second embodiment, the invention is a method of treating an ear infection, said method comprising insertion of a tympanostomy tube in an ear drum by myrangotomy, said tympanostomy tube being comprised of a solid, non-porous composite comprised of:
  a) a melt blend of:
    (i) an ethylene-vinyl acetate copolymer having a melt index less than about 50 g/10 min. as measured by ASTM D1238 and comprising 10 to 50 percent by weight of vinyl acetate,
    (ii) polyethylene glycol having a weight average molecular weight of from about 2,000 to about 20,000 Daltons; and b) one or more bioactive agents comprising at least ciprofloxacin antibiotic dispersed uniformly throughout said polymer material; said bioactive agents comprising about 1 to about 60 percent by weight of said polymer plus bioactive agents
wherein said ciprofloxacin is present in said polymer material as:
i) a solid solution phase with said polymer material comprised of from about 0.1 to about 30 percent by weight of said ciprofloxacin; and
ii) a solid solution phase with said polymer material comprised of from about 95 to about 99.99 percent by weight of said ciprofloxacin; and
iii) a phase selected from a supersaturated solution, essentially pure ciprofloxacin, a solid solution comprised of ciprofloxacin and their combination.

BRIEF DESCRIPTION OF THE DRAWINGS

FIG. 18 is a plot showing the bacterial count on the tympanostomy tubes after transbullar challenge and removal from the animals in Example 22.

DETAILED DESCRIPTION OF THE INVENTION

Figure 1:
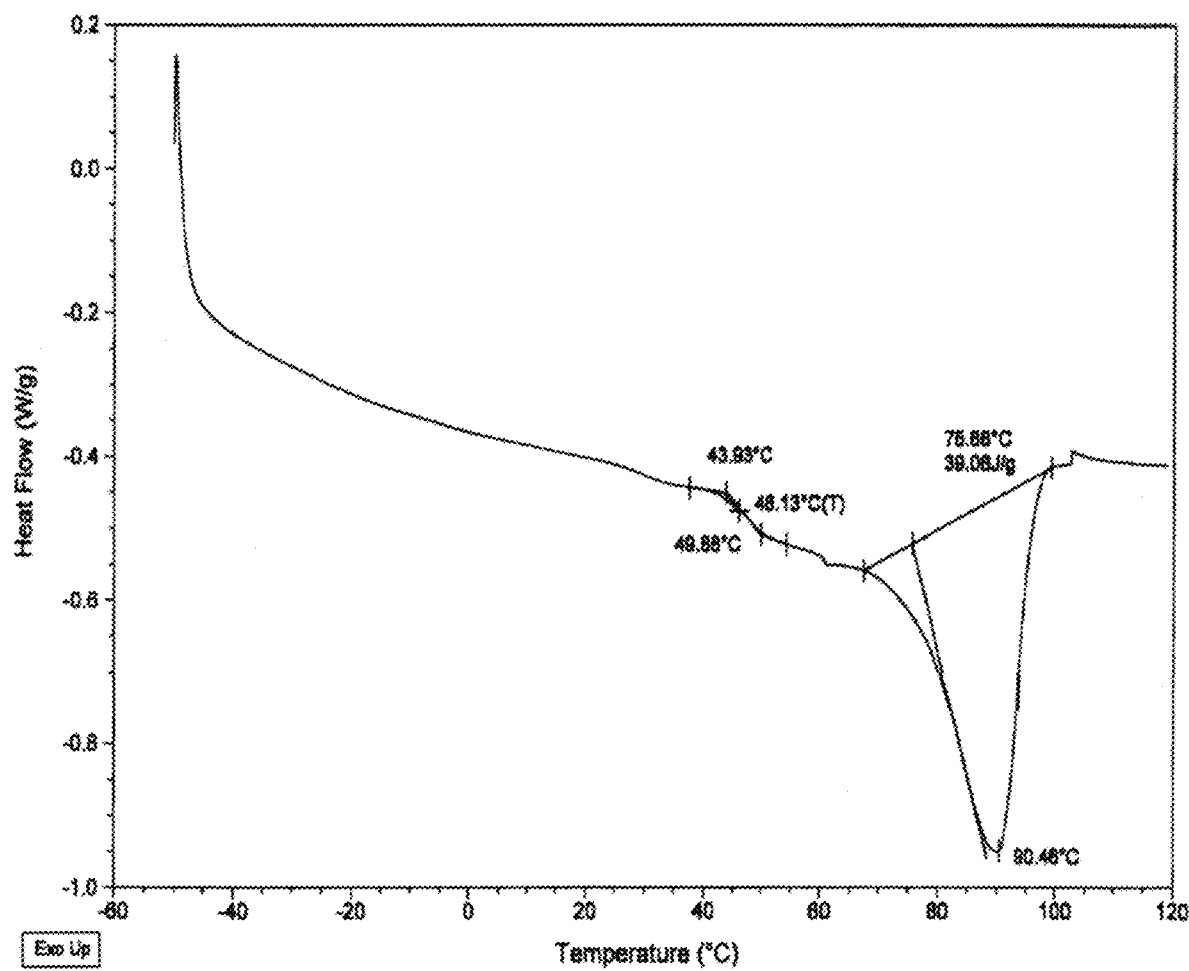
FIG. 1 is a DSC scan of an ethylene-vinyl acetate copolymer containing 18% by weight of vinyl acetate.

In a first embodiment, the invention is a method of preventing an ear infection, said method comprising insertion of a tympanostomy tube in an ear drum by myrangotomy, said tympanostomy tube being comprised of a solid, non-porous composite comprised of:
a) a melt blend of:
(i) an ethylene-vinyl acetate copolymer having a melt index less than about 50 g/10 min. as measured by ASTM D1238 and comprising 10 to 50 percent by weight of vinyl acetate,
(ii) polyethylene glycol having a weight average molecular weight of from about 2,000 to about 20,000 Daltons; and
b) one or more bioactive agents comprising at least ciprofloxacin antibiotic dispersed uniformly throughout said polymer material; said bioactive agents comprising about 1 to about 60 percent by weight of said polymer plus bioactive agents;
wherein said ciprofloxacin is present in said polymer material as:
i) a solid solution phase with said polymer material comprised of from about 0.1 to about 30 percent by weight of said ciprofloxacin; and
ii) a solid solution phase with said polymer material comprised of from about 95 to about 99.99 percent by weight of said ciprofloxacin; and
iii) a phase selected from a supersaturated solution, essentially pure ciprofloxacin, a solid solution comprised of ciprofloxacin and their combination.

The inventive method of prevention is particularly useful against acute or chronic otitis media.

Preferably, the ciprofloxacin employed in the invention, before dispersion in the polymer material, has a particle size distribution best described by a Weibull function with an index of determination of at least about 0.90, said distribution having a characteristic size of from about 5 to about 100 micrometers and a shape factor from about 1.1 to about 5.

In a second embodiment, the invention is a method of treating an ear infection, said method comprising insertion of a tympanostomy tube in said ear drum or tympanic membrane by myrangotomy, said tympanostomy tube being comprised of a solid, non-porous composite comprised of:
a) a melt blend of:
(i) an ethylene-vinyl acetate copolymer having a melt index less than about 50 g/10 min. as measured by ASTM D1238 and comprising 10 to 50 percent by weight of vinyl acetate,
(ii) polyethylene glycol having a weight average molecular weight of from about 2,000 to about 20,000 Daltons; and
b) one or more bioactive agents comprising at least ciprofloxacin antibiotic dispersed uniformly throughout said polymer material; said bioactive agents comprising about 1 to about 60 percent by weight of said polymer plus bioactive agents;
wherein said ciprofloxacin is present in said polymer material as:
i) a solid solution phase with said polymer material comprised of from about 0.1 to about 30 percent by weight of said ciprofloxacin; and
ii) a solid solution phase with said polymer material comprised of from about 95 to about 99.99 percent by weight of said ciprofloxacin; and
iii) a phase selected from a supersaturated solution, essentially pure ciprofloxacin, a solid solution comprised of ciprofloxacin and their combination.

The inventive method of treatment is particularly useful against acute or chronic otitis media.

In comparison with the prior art, the inventive methods employ inventive articles comprised of three phases of ciprofloxacin anti-biotic agent.

Preferably, the ciprofloxacin employed in an embodiment of the Invention, before dispersion in the polymer material, has a particle size distribution best described by a Weibull function with an index of determination of at least about 0.90, said distribution having a characteristic size of from about 5 to about 100 micrometers and a shape factor from about 1.1 to about 5.

The expression "a particle size distribution best described by a Weibull function" means that regression of particle sizes against a Weibull function of the particle sizes yields an index of determination that is greater than the index of determination obtained by regression with any one of: a normal distribution, a log normal distribution, an exponential distribution, or an extreme value distribution.

A Weibull distribution of particle sizes is described by the following relationship:

$$F(d) = 1 - e^{-\left(\frac{d}{D}\right)^S} \qquad \text{Eq. 1}$$

where:
d is the particle size, microns
e is the base of natural logarithms, equal to 2.71828 approximately
F(d) is the cumulative size fraction of particles smaller than d
D is a characteristic size for the distribution, microns
S is a shape factor for the distribution, dimensionless For a Weibull particle size distribution, a plot of log(d) versus log [ln(1/(1−F(d)))] is a straight line having a slope of 1/S and having an intercept of log(D). The index of determination is found by regression analysis of log(d) versus log [ln(1/(1−F))]. Preferably, the index of determination is at least about 0.92. More preferably, the index of determination is at least about 0.94, yet more preferably at least about 0.96, and most preferably at least about 0.98.

If a ciprofloxacin powder is not available having a desired Weibull particle size distribution, one can be created from a powder having some other initial particle size distribution. The man of ordinary skill in the art will pass the powder through a series of screens of increasingly finer mesh size, and then combine the collected size fractions in appropriate proportions. Grinding or milling beforehand may be employed to increase the proportion of finer particles, or any one of several agglomeration techniques known in the art may be employed beforehand to increase the proportion of larger particles.

Preferably, ciprofloxacin used in an embodiment of the invention has a Weibull particle size distribution with a characteristic size of from about 10 to about 100 micrometers and a shape factor from about 1.2 to about 4. More preferably, the Weibull particle size distribution has a characteristic size of from about 10 to about 75 micrometers and a shape factor from about 1.2 to about 3.5. Most preferably, the Weibull particle size distribution has a characteristic size of from about 10 to 40 micrometers and a shape factor from about 1.3 to about 3.

Preferably, a composite employed in an embodiment of the invention contains from about 1 to about 30 percent by weight of ciprofloxacin. More preferably, a composite employed in the invention contains from about 1 to about 25 percent by weight of ciprofloxacin.

Preferably, additional bioactive agents are selected from the group consisting of anti-biotic agents and anti-inflammatory agents. Preferably, anti-biotic agents are selected from the group consisting of carbapenems, cephalosporins, penicillins, lincosamides, tetracyclins, macrolides, glycopeptides, quinolones, oxazolidinones, aminoglycosides gyrase inhibitors, and their combination.

More preferably, anti-biotic agents are selected from the group consisting of beta lactam, meropenem, ceftazidime, amoxicillin, clindamycin, tetracycline, erythromycin, vancomycin, ciprofloxacin, linezolid, usnic acid, polyhexamethylene biguanide, N-acetylcysteine, rifampicin, minocycline and their combination.

Most preferably, anti-biotic agents are selected from the group consisting of usnic acid, sodium usnate, polyhexamethylene biguanide, polyhexamethylene biguanide hydrochloride and their combination.

Preferably, the anti-inflamatory agent is a glucocorticoid. More preferably, the anti-inflammatory agent is selected from the group consisting of dexamethasone dispropionate, clobetasol propionate and hydrocortisone.

Preferably, the anti-biotic agents employed in the invention have less than about 2.5 percent weight loss at a temperature of 200° C. when measured in a pure state by thermogravimetric analysis at a heating rate of 10° C./min, and more preferably less than about one percent weight loss.

The anti-biotic agents employed in the invention are preferably crystalline solids in powder form. A composite material employed in the invention may contain less than about 25 percent by weight of materials commonly used in polymers selected from the group consisting of plasticizers, colorants, anti-oxidant, stabilizers, processing aids, surfactants and fillers.

A composite of the invention containing an antibiotic is useful in protecting a device against colonization or formation of a biofilm by organisms selected from the genera consisting of *Corynebacterium, Enterococcus, Escherichia, Haemophilus, Mycoplasma, Neisseria, Pseudomonas, Staphylococcus, Streptococcus, Campylobacter, Propionobacterium, Klebsiella, Enterobacter, Bacillus, Burkholderia, Mycobacterium, Clostridium, Legionella, Listeria, Salmonella, Vibrio, Candida*, and their combination.

There is a high Incidence of ear Infections of the middle ear known as otitis media with effusion in infants and small children, To treat this condition, a small device known as a tympanostomy tube (TT), or ear tube is surgically Implanted in the tympanic membrane of the child. The surgical procedure used to implant ear tube is known as myrangotomy, and is the most frequent surgery performed in the United States. In the case of ongoing effusion, also known as otorrhea, of liquid or pus from the middle ear, the TT can serve to equalize pressure between the middle and outer ear, and provide a conduit for drainage. In an attempt to manage this disease, it Is important to control both the frequency and duration of otorrhea.

Unfortunately, there is an unmet difficulty with present TT devices. Over time, a biofilm may form on the surface of the TT, which would become a nidus for recurrent infections. The small (0.9 mm) lumen of the TT may become blocked and become the site for persistent infection. The biofilm consists of bacterial cells embedded in a protective host film comprised of extracellular materials such as polysaccharides and proteins. However, in contrast with existing devices, a tympanostomy tube prepared from a composite of the present invention provides sufficient antibiotic to prevent or minimize biofilm formation over an extended period.

The formation of a phase structure wherein two distinct solid-solution phases of anti-biotic agent and polymer coexist with un-dissolved anti-biotic agent requires chemical affinity between the anti-biotic agent and the polymer. Additionally, it is believed that satisfaction of two necessary but not sufficient process conditions must be met. First, the anti-biotic agent and polymer must be combined in the polymer melt at elevated temperature, and second, the molten state must be maintained for sufficient time for solution phase to form. Preferably, the fluxed polymer and anti-biotic agents are subjected to elevated temperature and shear for at least about 1 minute, preferably at least about 2 minutes, more preferably at least about 5 minutes, yet more preferably at least about 10 minutes, and most preferably, at least about 15 minutes.

EXAMPLES

The following examples are presented to provide a more complete understanding of the invention. The specific techniques, conditions, materials, proportions and reported data set forth to illustrate the principles of the invention are exemplary and should not be construed as limiting the scope of the invention Example 1

A solid thermoplastic polymer material was selected consisting of an ethylene-vinyl acetate copolymer (hereinafter referred to as an "EVA") containing 18% by weight of vinyl acetate (VA). The EVA from E.I DuPont, designated ELVAX™ 560, had a melt index of 2.5 g/10 minutes as measured by ASTM D 1238. A 1.6 mm thick disk of this EVA had 0.28 percent by weight of dissolution in distilled water at 35° C. in 30 days. The EVA is non-biodegradable. Devices comprised of EVA have been approved by the United States Food and Drug Administration for implantation in a living mammal. A differential scanning calorimetry (DSC) scan of the melting of this EVA at a heating rate of 10° C./min is shown in FIG. 1. The pure EVA melted over a temperature range of 67° C. to 98° C.

Figure 2:
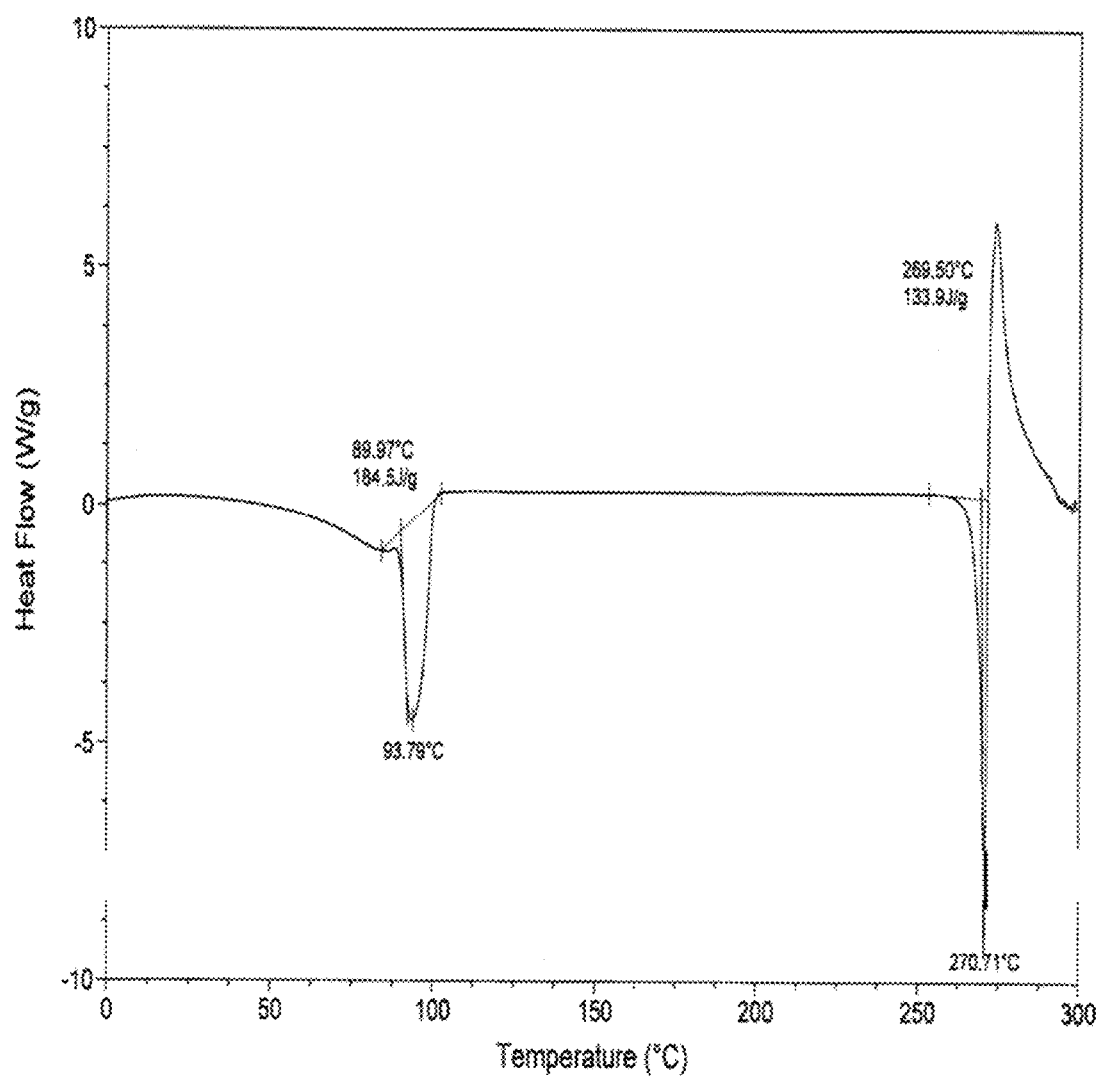
FIG. 2 is a DSC scan of ciprofloxacin.

An anti-biotic agent was selected consisting of ciprofloxacin betaine crystalline powder (C.A.S. Registry No. 85721-33-1). Ciprofloxacin is a broad spectrum antimicrobial agent having less than 1 percent weight loss at a temperature of 250° C. when measured in a pure state by thermogravimetric analysis at a heating rate of 10° C./min. A DSC scan of the melting of this ciprofloxacin powder at a heating rate of 10° C./min is shown in FIG. 2. The ciprofloxacin melted over a temperature range of 252° C. to 271° C.

Figure 3:
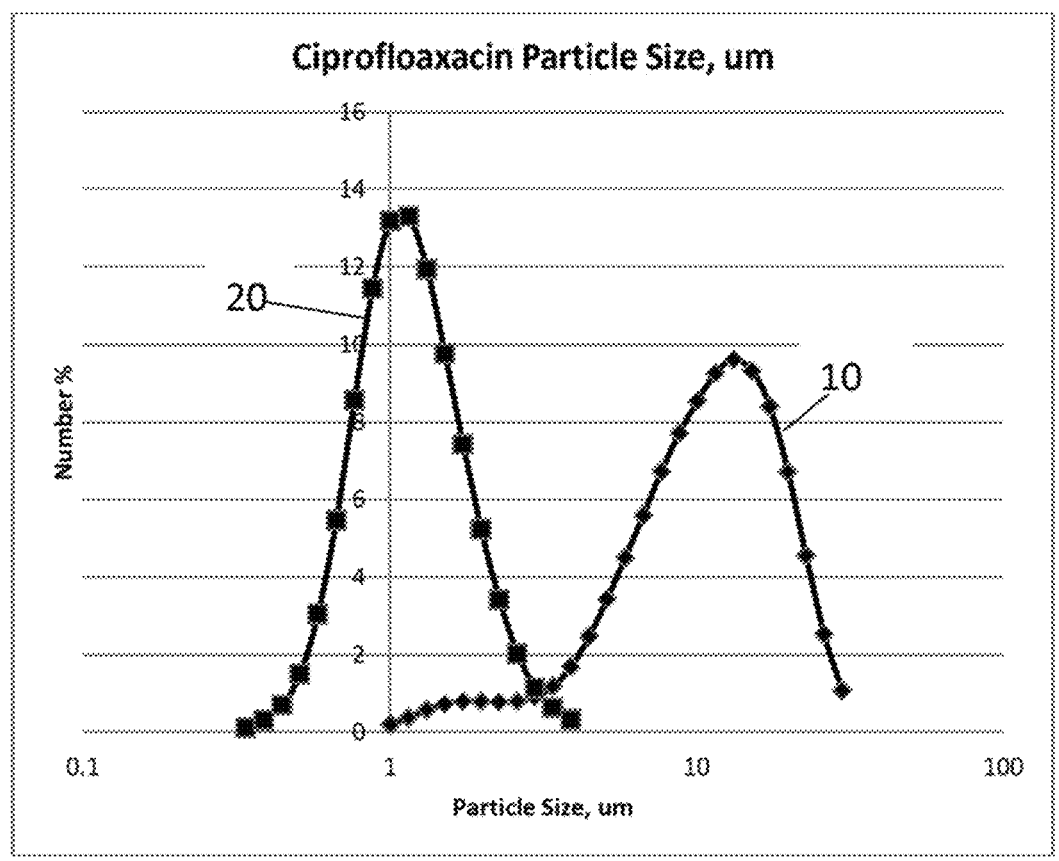
FIG. 3 is a plot of the particle size distributions of the crystalline ciprofloxacin material used in the examples.
Figure 4:
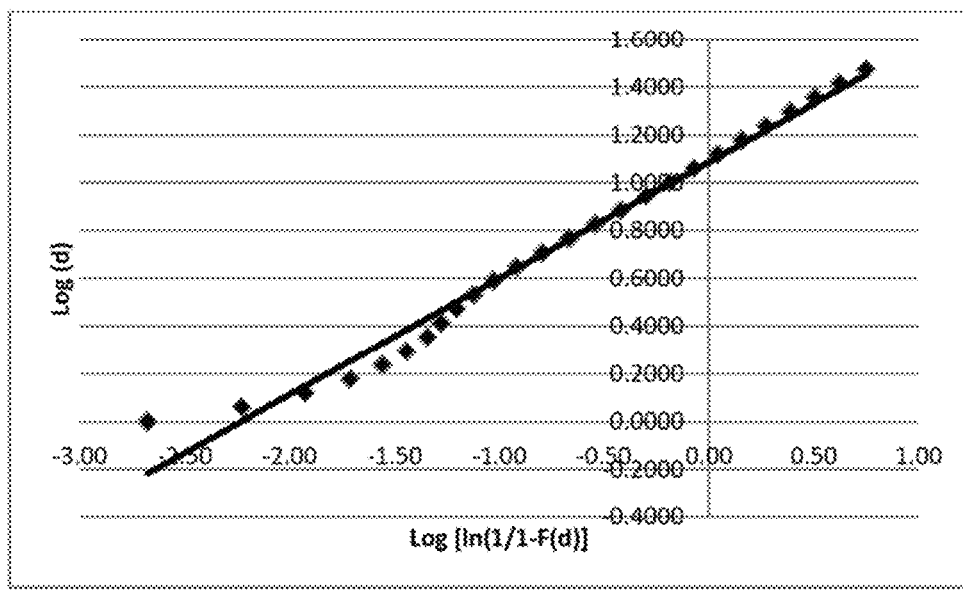
FIG. 4 is a Weibull plot of the particle size distribution of a crystalline ciprofloxacin bioactive agent used in the examples of the invention.

The selected ciprofloxacin was further characterized by use of a Horiba Instruments, Inc Model LA-900 Laser Scattering Particle Size Distribution Analyzer. This instrument measures the volume of particles having a size between selected upper and lower limits. The selected ciprofloxacin powder had particle size distribution best described by a Weibull function with an index of determination of 0.991, a characteristic size of 12.25 micrometers, and a shape factor of 2.054. The particle size distribution of the selected ciprofloxacin is given in Table I below, and is plotted as line 10 in FIG. 3. A Weibull plot of this particle size distribution conforming to the invention is shown in FIG. 4.

35 grams of the selected EVA was charged to the mixing chamber of a Brabender Plasticorder preheated to a temperature of 185° C. The mixing chamber of the Brabender Plasticorder was equipped with two sigma-style co-rotating blades and had a capacity of 45 cm³. The EVA was melted at a mixing speed of 35 rpm under a flow of dry nitrogen.

When the EVA had completely melted, 6.176 grams (15.0 percent by weight) of the selected ciprofloxacin betaine powder was added gradually to the mixer. After adding the ciprofloxacin, the speed of the mixer was Increased to 60 RPM for 10 minutes to produce a uniform mixture of the ciprofloxacin in the EVA copolymer melt.

The mixer was turned off and the ciprofloxacin/EVA mixture was removed from the mixer, transferred to a glass container and cooled to room temperature under ambient conditions to solidify into a solid, non-porous composite material of the invention.

Optical microscopy of this composite material of the invention showed the presence of a dispersed phase of ciprofloxacin particles.

Figure 5:
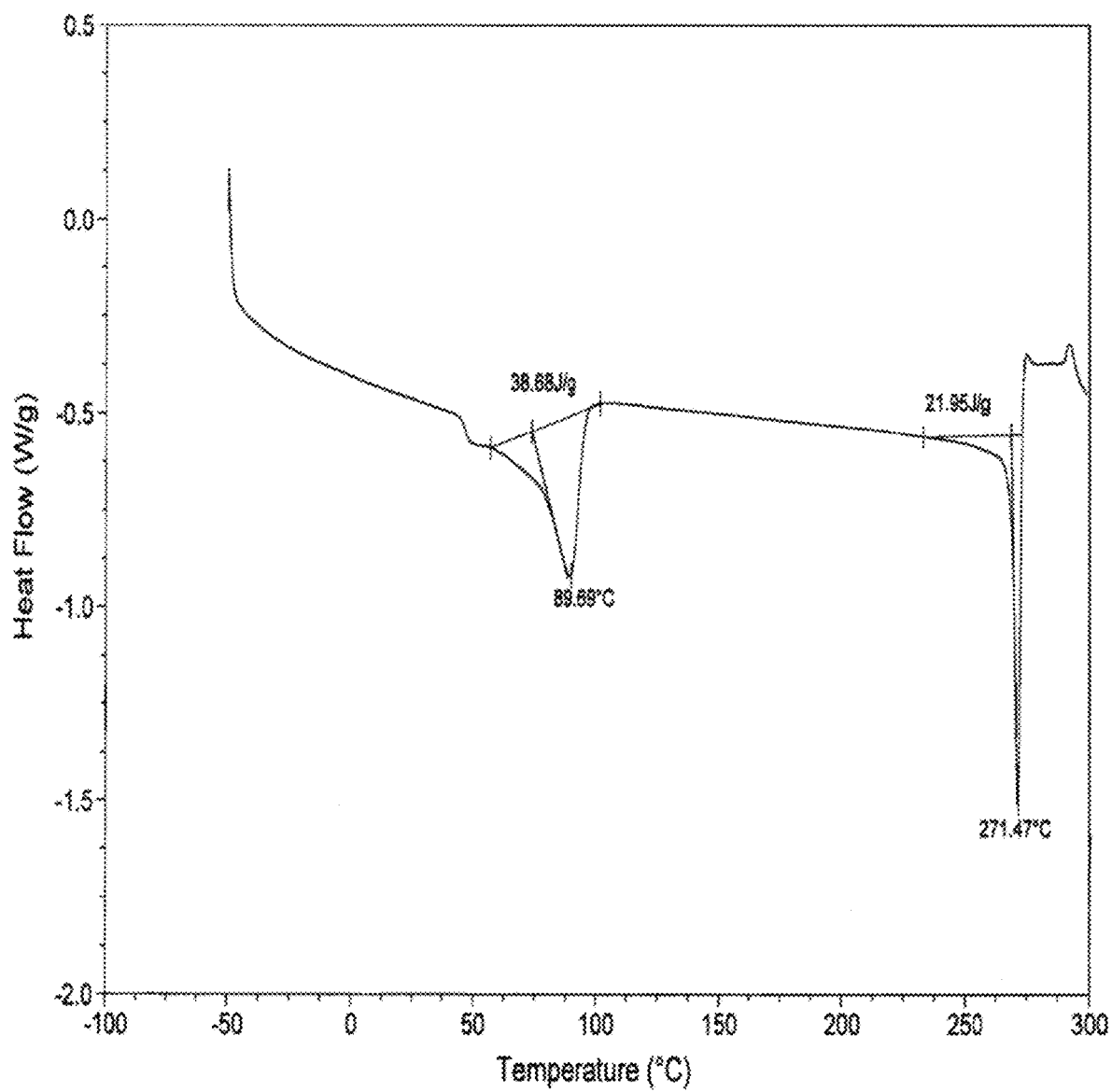
FIG. 5 is a DSC scan of a composite of the invention.

A DSC scan of this composite material of the invention at a heating rate of 10° C./min is shown in FIG. 5. The DSC scan shows melting of the EVA phase over the temperature range of 52° C. to 98° C.: a lower onset and broadening of its melting range compared to the pure EVA. The DSC scan of FIG. 5 also shows melting of the ciprofloxacin phase over the temperature range of 232° C. to 273° C.: again a lower onset and broadening of its melting range compared to the pure ciprofloxacin material. These lower onsets and broadening of the melting ranges of both the EVA and the ciprofloxacin, indicate the presence in the composite of: 1) a solid solution phase of ciprofloxacin in EVA, and 2) a solid solution phase of EVA in ciprofloxacin in addition to the un-dissolved ciprofloxacin particles. It is estimated that the solid solution of ciprofloxacin in EVA contained less than about 1 percent by weight of ciprofloxacin, and the solid solution of EVA in ciprofloxacin contained less than about 1 percent by weight of EVA. Such phases most likely exist as surface layers covering the ciprofloxacin particles and accordingly they are expected to influence the drug dissolution rates.

Moreover, the presence of solid solution phases at the phase boundaries is believed to be responsible for greater physical integrity of the composite material. The composites of the invention withstand immersion in aqueous media indefinitely without evident disintegration.

Example 2

40 grams of the same EVA containing 18 wt. % vinyl acetate as described in Example 1 was charged to the mixing chamber of the some Brabender Plasticorder as described in Example 1 preheated to a temperature of 185° C. The EVA was melted at a mixing speed of 35 rpm under a flow of dry nitrogen.

When the EVA had completely melted, 1.237 grams (3.00 percent by weight) of the same ciprofloxacin powder as described in Example 1 was added gradually to the mixer. The speed of the mixer was increased to 60 RPM for 10 minutes to produce a uniform dispersion of the ciprofloxacin powder in the EVA melt.

The mixer was turned off and the ciprofloxacin/EVA dispersion was removed from the mixer, transferred to a glass container and cooled to room temperature under ambient conditions to solidify into a solid, non-porous composite material of the invention.

Optical microscopy of this composite material of the invention showed the presence of a dispersed phase of un-dissolved ciprofloxacin particles. DSC determination of the phases present was not done, but it is believed that two solid-solution phases of ciprofloxacin/EVA were formed as in Example 1.

This experiment was repeated with different grades of EVA having different percentage of vinyl acetate content. The results were essential similar.

Example 3

34.47 grams of the same EVA containing 18 wt. % vinyl acetate described in Example 1 and 5.53 grams of polyethylene glycol (PEG) were charged to the mixing chamber of the same Brabender Plasticorder as described in Example 1 preheated to a temperature of 175° C. The PEG from Sigma-Aldrich had a molecular weight of 8000 Daltons. The EVA copolymer and polyethylene glycol were melted at a mixing speed of 35 rpm under a flow of dry nitrogen.

When the EVA and PEG had completely melted, 2.553 grams (6.00 percent by weight) of the same ciprofloxacin powder as described in Example 1 was added gradually to the mixer. The speed of the mixer was increased to 60 RPM for 10 minutes to produce a uniform dispersion of the ciprofloxacin powder in the EVA and PEG melt.

The mixer was turned off and the ciprofloxacin/polymer dispersion was removed from the mixer, transferred to a glass container and cooled to room temperature under ambient conditions to solidify into solid, non-porous composite material of the invention.

Optical microscopy of this composite material of the invention showed the presence of a dispersed phase of ciprofloxacin particles. While differential scanning calorimetry was not performed on this composite, it is believed that two solid-solution phases of ciprofloxacin/EVA and EVA/ciprofloxacin were present here as in the composite of Example 1 A control sample was prepared consisting only of the EVA and PEG in the same proportions as above but without any ciprofloxacin. A 1.6 mm thick disk of this material showed less than 1% dissolution in distilled water at 35° C. in 30 days.

Example 4

35 grams of the same EVA copolymer containing 18 wt. % vinyl acetate as described in Example 1 was charged to the mixing chamber of the same Brabender Plasticorder as described in Example 1 preheated to a temperature of 185° C.

The ciprofloxacin betaine powder employed had a particle size distribution best described by a log normal distribution with an index of determination of 0.998 a mean of 1.11 micrometers and a standard deviation of 0.180 micrometers. The particle size distribution of this ciprofloxacin powder is given in Table I below, and is plotted as line 20 in FIG. 3.

When the EVA had completely melted, 6.176 grams (15.0 percent by weight) of this ciprofloxacin powder was added gradually to the mixer. The speed of the mixer was increased to 60 RPM for 10 minutes to produce a uniform dispersion of the ciprofloxacin powder in the EVA melt.

The mixer was turned off and the ciprofloxacin/EVA dispersion was removed from the mixer, transferred to a glass container and cooled to room temperature under ambient conditions to solidify into a solid, non-porous composite material of the invention.

Optical microscopy of this composite material of the invention showed the presence of a dispersed phase of un-dissolved ciprofloxacin particles. DSC determination of the phases present was not done, but it is believed that two solid-solution phases of ciprofloxacin/EVA were formed here as in Example 1.

Example 5

40 grams of an EVA containing 32 wt. % vinyl acetate designated ELVAX™ 150 having a melt index of 43 g/10 min. as measured by ASTM D 1238 was charged to the mixing chamber of the same Brabender Plasticorder as described in Example 1 preheated to a temperature of 140° C. The EVA was melted at a mixing speed of 35 rpm under a flow of dry nitrogen.

When the EVA had completely melted, 1.237 grams (3.00 percent by weight) of the same ciprofloxacin powder as described in Example 4 was added gradually to the mixer. The speed of the mixer was increased to 50 RPM for 20 minutes to produce a uniform dispersion of the ciprofloxacin powder in the EVA melt.

The mixer was turned off and the ciprofloxacin/EVA dispersion was removed from the mixer, transferred to a glass container and cooled to room temperature under ambient conditions to solidify into a solid, non-porous composite material of the invention.

Optical microscopy of this composite material of the invention showed the presence of a dispersed phase of un-dissolved ciprofloxacin particles. DSC determination of the phases present was not done, but it is believed that two solid-solution phases of ciprofloxacin/EVA were formed as in Example 1.

A control sample of this same EVA was prepared consisting of a 1.6 mm thick disk. The disk showed 0.20 percent by weight of dissolution in distilled water in 30 days at 35° C.

TABLE I

Particle Size Distributions of Ciprofloxacin

| d, Particle Size, um | Volume % | |
|---|---|---|
| | Examples 1-3 | Examples 4-5 |
| 0.339 | | 0.12 |
| 0.388 | | 0.31 |
| 0.445 | | 0.71 |
| 0.509 | | 1.52 |
| 0.582 | | 3.05 |
| 0.668 | | 5.49 |
| 0.765 | | 8.57 |
| 0.877 | | 11.44 |
| 1.004 | 0.2 | 13.2 |
| 1.15 | 0.38 | 13.31 |
| 1.318 | 0.58 | 11.95 |
| 1.509 | 0.74 | 9.78 |
| 1.729 | 0.81 | 7.44 |
| 1.98 | 0.8 | 5.26 |
| 2.268 | 0.79 | 3.42 |
| 2.598 | 0.8 | 2.04 |
| 2.976 | 0.91 | 1.16 |
| 3.408 | 1.2 | 0.64 |
| 3.904 | 1.71 | 0.34 |
| 4.472 | 2.48 | |
| 5.122 | 3.44 | |
| 5.866 | 4.52 | |
| 6.719 | 5.61 | |
| 7.696 | 6.73 | |
| 8.815 | 7.73 | |
| 10.09 | 8.55 | |
| 11.56 | 9.26 | |
| 13.24 | 9.62 | |
| 15.17 | 9.33 | |

TABLE I-continued

Particle Size Distributions of Ciprofloxacin

| d, Particle Size, um | Volume % | |
|---|---|---|
| | Examples 1-3 | Examples 4-5 |
| 17.37 | 8.41 | |
| 19.9 | 6.72 | |
| 22.79 | 4.57 | |
| 26.11 | 2.54 | |
| 29.9 | 1.1 | |

Example 6

The composite material of the invention prepared in Example 2 was compression molded at a temperature of 175° C. into disks having dimensions of 0.16 cm thickness and 1.25 cm diameter. The initial weight of ciprofloxacin in the disks was known from the concentration of ciprofloxacin in the composite material and the measured weight of the disks. The disks were placed in sample vials with 15.0 ml of distilled water at 22° C.±2° C. Racks of vials were agitated. The distilled water was replaced at intervals of one day. The concentration, and from that, the weight of ciprofloxacin in the water was determined using a Beckman DU-530 UV-vis spectrophotomer. The cumulative weight of ciprofloxacin released was determined by summing the weights for each interval. The cumulative percent of the initial weight of the ciprofloxacin anti-biotic agent, ($M_t$) released from the disk into the water is given in Table II below and plotted as line 30 in FIG. 6. The measurements were terminated after 31 days.

Figure 7:
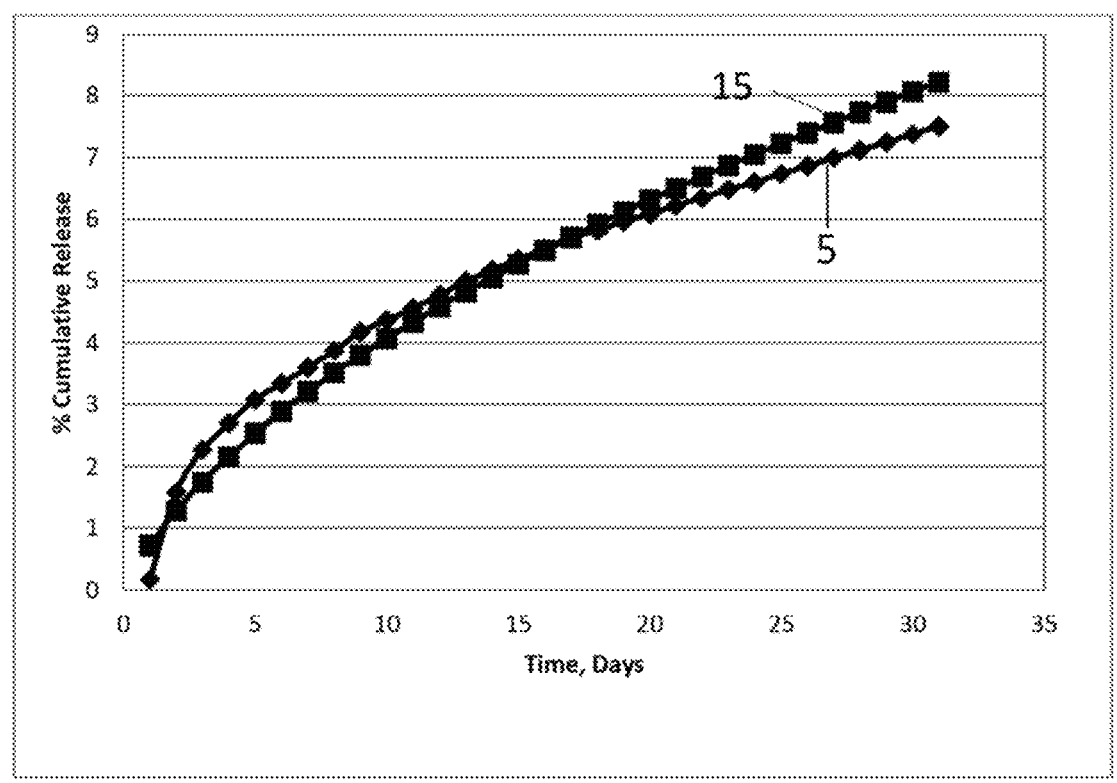
FIG. 7 is a plot of calculated and observed cumulative release of bioactive agent as a percentage of the Initial bioactive content as a function of time for Example 6.

The cumulative percentage release of ciprofloxacin was described by Equation 2 below with a maximum deviation of less than 20% over the period from day 2 to day 30:

$$M_t = 1.8181\sqrt{1+0.95t} - 1.8181 \qquad \text{Eq. 2}$$

where: $M_t$ is the cumulative weight of anti-biotic agent released divided by the initial weight of anti-biotic agent weight×100;

t is time in days.

in FIG. 7. The observed cumulative percentage release of ciprofloxacin (5) is compared with that calculated (15) from Eq. 2

Surprisingly, it may be seen from Table ii that the release of ciprofloxacin from the composite of the invention was essentially constant at 0.13±0.01% per day over the period from 18 to 31 days. The rate of change of release rate over this period was less than 0.05% per day per day. Extended, essentially constant, drug release was obtained over this period. Without being held to a particular explanation, it is believed that this useful drug release profile was related to the unique Weibull particle size distribution of the drug and/or the unique phase structure of the composite.

Example 7

The composite material of the invention prepared in Example 3 was compression molded at a temperature of 175° C. into disks having dimensions of 0.16 cm thickness and 1.25 cm diameter. The disks were weighed and placed in distilled water as in Example 2. The weight of ciprofloxacin extracted each day and the cumulative weight extracted was measured as in Example 2. The cumulative percent of the Initial weight of the ciprofloxacin anti-biotic agent, ($M_t$) released from the disk into the water is given in Table ii below and plotted as line 40 in FIG. 6.

The cumulative percentage release of ciprofloxacin was described by Equation 3 below with a maximum deviation of less than 20% over the period from day 2 to day 30:

$$M_t = 3.2\sqrt{1+0.1t} - 3.2 \qquad \text{Eq. 3}$$

Where: $M_t$ is the cumulative weight of anti-biotic agent released divided by the initial weight of anti-biotic agent weight×100;

t is time in days.

Figure 8:
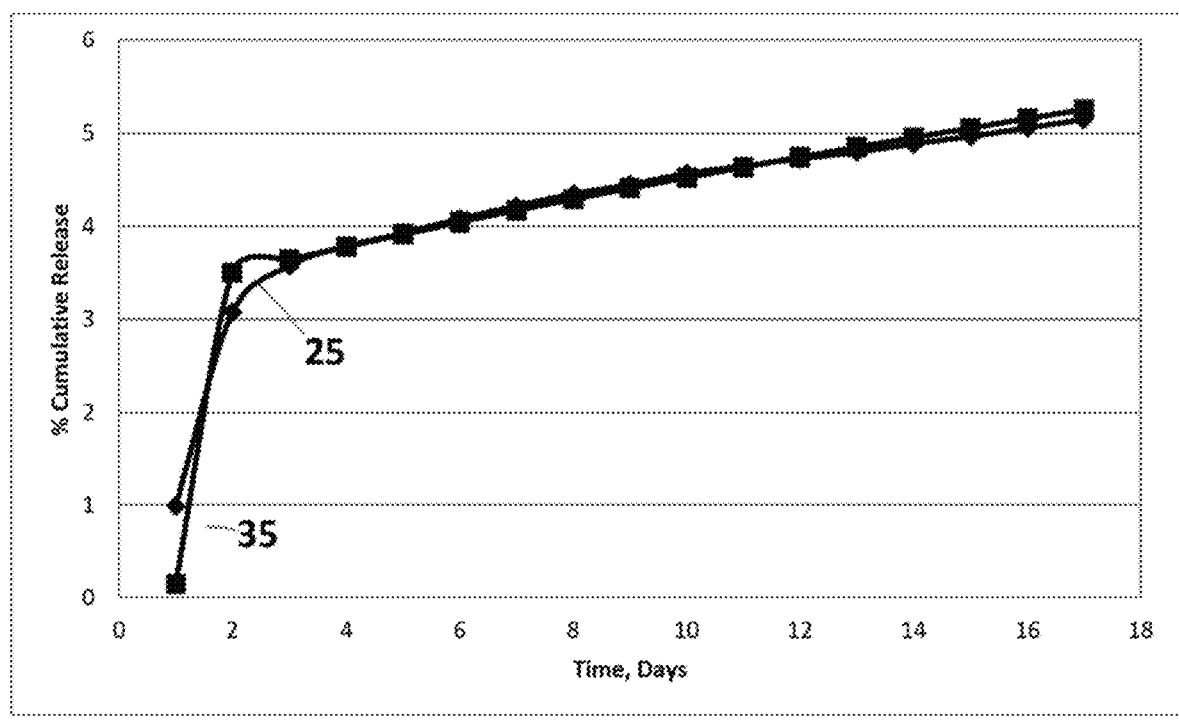
FIG. 8 is a plot of calculated and observed cumulative release of bioactive agent as a percentage of the initial bioactive content as a function of time for Example 7.

The observed (25) cumulative percentage release of ciprofloxacin is compared with that calculated (35) from Eq. 3 in FIG. 8. Surprisingly, it may be seen from Table II or from Eq. 3 that the rate of release of ciprofloxacin from the composite of the invention was essentially constant at 0.08±0.01% per day over the period from 11 to 17 days. Extended, essentially constant, drug release was obtained over this period.

Example 8

The material prepared in Example 4 was compression molded at a temperature of 175° C. into disks having dimensions of 0.16 cm thickness and 1.25 cm diameter. The disks were weighed and placed in distilled water as in Example 2. The weight of ciprofloxacin extracted each day and the cumulative weight extracted was measured as in Example 2. The concentration, and from that, the weight of ciprofloxacin in the water was determined using a Beckman DU-530 UV-vis spectrophotomer. The cumulative weight of ciprofloxacin released was determined by summing the weights for each interval. The cumulative percent of the initial weight of the ciprofloxacin anti-biotic agent released from the disk into the water is given in Table II below and is plotted as line 50 in FIG. 6.

Example 9

The material prepared in Example 5 was compression molded at a temperature of 175° C. into disks having dimensions of 0.16 cm thickness and 1.25 cm diameter. The disks were weighed and placed in distilled water as in Example 2. The weight of ciprofloxacin extracted each day and the cumulative weight extracted was measured as in Example 2. The concentration, and from that, the weight of ciprofloxacin in the water was determined using a Beckman DU-530 UV-vis spectrophotomer. The cumulative weight of ciprofloxacin released was determined by summing the weights for each interval. The cumulative percent of the initial weight of the ciprofloxacin anti-biotic agent released from the disk into the water is given in Table II below and is plotted as line 60 in FIG. 6. For clarity, the designation 18 wt. % VA/EVA refers to an ethylene-vinyl acetate copolymer (EVA) containing 18 wt. % vinyl acetate (VA).

TABLE II

| | $M_t$, Cumulative % of Initial Ciprofloxacin Released | | | |
|---|---|---|---|---|
| | Example 6 3 wt. % ciprofloxacin 18 wt. % VA/EVA Weibull Particle Dist. | Example 7 6 wt. % ciprofloxacin 18 wt. % VA/EVA Weibull Particle Dist. | Example 8 15 wt. % ciprofloxacin 18 wt. % VA/EVA Log Normal Particle Dist. | Example 9 3 wt. % ciprofloxacin 32 wt. % VA/EVA Log Normal Particle Dist. |
| 1 | 0.176 | 0.99 | 0.098 | 0.058 |
| 2 | 1.58 | 3.08 | 0.14 | 0.15 |
| 3 | 2.28 | 3.58 | 0.15 | 0.2 |

TABLE II-continued $M_t$, Cumulative % of Initial Ciprofloxacin Released

| | Example 6<br>3 wt. % cip-<br>rofloxacin<br>18 wt. %<br>VA/EVA<br>Weibull<br>Particle Dist. | Example 7<br>6 wt. % cip-<br>rofloxacin<br>18 wt. %<br>VA/EVA<br>Weibull<br>Particle Dist. | Example 8<br>15 wt. % cip-<br>rofloxacin<br>18 wt. %<br>VA/EVA<br>Log Normal<br>Particle Dist. | Example 9<br>3 wt. % cip-<br>rofloxacin<br>32 wt. %<br>VA/EVA<br>Log Normal<br>Particle Dist. |
|---|---|---|---|---|
| 4 | 2.7 | 3.79 | 0.16 | 0.24 |
| 5 | 3.08 | 3.93 | 0.17 | 0.26 |
| 6 | 3.34 | 4.08 | 0.17 | 0.28 |
| 7 | 3.6 | 4.22 | 0.17 | 0.29 |
| 8 | 3.88 | 4.35 | 0.17 | 0.32 |
| 9 | 4.18 | 4.45 | 0.17 | 0.35 |
| 10 | 4.37 | 4.57 | 0.17 | 0.37 |
| 11 | 4.56 | 4.65 | 0.17 | 0.39 |
| 12 | 4.78 | 4.73 | 0.17 | 0.41 |
| 13 | 5 | 4.8 | 0.17 | 0.42 |
| 14 | 5.18 | 4.89 | 0.17 | 0.44 |
| 15 | 5.36 | 4.97 | 0.17 | 0.46 |
| 16 | 5.52 | 5.06 | 0.17 | 0.47 |
| 17 | 5.7 | 5.15 | 0.17 | 0.48 |
| 18 | 5.82 | In process | 0.17 | 0.49 |
| 19 | 5.96 | | 0.17 | 0.51 |
| 20 | 6.08 | | 0.17 | 0.52 |
| 21 | 6.22 | | 0.17 | 0.53 |
| 22 | 6.35 | | 0.17 | 0.54 |
| 23 | 6.48 | | 0.17 | 0.56 |
| 24 | 6.6 | | 0.17 | 0.57 |
| 25 | 6.74 | | 0.17 | 0.58 |
| 26 | 6.86 | | 0.17 | 0.59 |
| 27 | 7 | | 0.17 | 0.6 |
| 28 | 7.12 | | 0.17 | 0.62 |
| 29 | 7.25 | | 0.17 | 0.62 |
| 30 | 7.38 | | 0.17 | 0.62 |
| 31 | 7.51 | | 0.17 | 0.62 |

Figure 6:
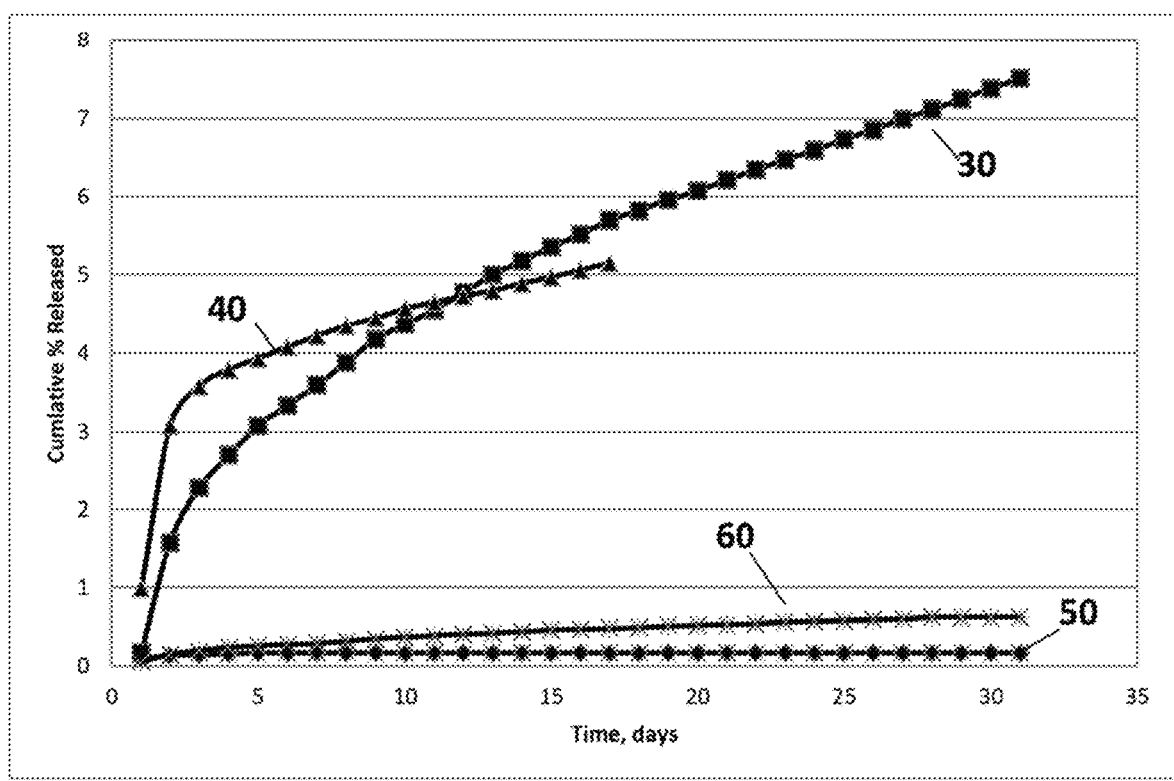
FIG. 6 is a plot of cumulative release of bioactive agent as a percentage of the initial bioactive content as a function of time for Examples 6 to 9.

Surprisingly, it will be seen from Table II or FIG. 6 the cumulative releases of anti-biotic agent were more than an order of magnitude higher in Examples 6 and 7 using an antibiotic having a Weibull particle size distribution than in Examples 8 and 9 where the antibiotic agent had a log normal particle size distribution. This is despite the fact that in Example 8 having the log normal particle size distribution, the antibiotic concentration was 2.5 to 5 fold higher than in the examples having a Weibull particle size distribution.

Example 10

A solid non-porous composite material of the invention was prepared as in Example 1 consisting of 81 percent by weight of the same ELVAX™ 560 EVA, 3 percent by weight of the same ciprofloxacin powder as in Example 1, 3 percent by weight of usnic acid (C.A.S. Registry No. 7562-61-0), and 3 percent by weight of polyhexamethylene biguanide hydrochloride (C.A.S. Registry No. 57028-96-3). Usnic acid and polyhexamethylene biguanide hydrochloride are anti-bacterial compounds.

This composite of the invention was molded into 6 mm diameter circular coupons. The coupons of each kind were placed on four Petri dishes containing LB broth, each freshly inoculated with a culture of one of: *Haemophilus* influenza, *Streptococcus pneumonia, Pseudomonas aeruginosa*, or *Staphylococcus aureus*, respectively. The cultures were incubated at a temperature of 37° C. to allow the bacteria to grow. At the end of five days, it was found that bacterial growth had been inhibited in zones measuring 7.5 mm, 4.5 mm, 7 mm, and 4.5 mm around the coupons respectively for the four organisms.

Example 11

25.2 grams of an EVA containing 32 wt. % vinyl acetate designated ELVAX™ 150 and 8.4 grams of polyethylene glycol (PEG) were charged to the mixing chamber of the same Brabender Plasticorder as described in Example 1 preheated to a temperature of 140° C. The PEG from Sigma-Aldrich had a molecular weight of 8000 Daltons. The EVA and polyethylene glycol were melted at a mixing speed of 35 rpm under a flow of dry nitrogen.

When the EVA and PEG had completely melted, 8.4 grams (20 percent by weight) of the same ciprofloxacin powder as described in Example 1 was added gradually to the mixer. The speed of the mixer was Increased to 50 RPM for 20 minutes to produce a uniform dispersion of the ciprofloxacin powder in the EVA and PEG melt.

The mixer was turned off and the ciprofloxacin/polymer dispersion was removed from the mixer, transferred to a glass container and cooled to room temperature under ambient conditions to solidify into solid, non-porous composite material of the invention.

Optical microscopy of this composite material of the invention showed the presence of a dispersed phase of ciprofloxacin particles. While differential scanning calorimetry was not performed on this composite, it is believed that two solid solution phases of ciprofloxacin/EVA and EVA/ciprofloxacin were present here as in the composite of Example 1.

A control sample was prepared consisting only of the same EVA and PEG in the same proportions as above but without any ciprofloxacin. A 1.6 mm thick disk of this material showed 0.26 percent by weight of dissolution in distilled water at 35° C. in 30 days.

Example 12

The composites of the invention described in Examples 1 to 5 and 11 were molded into 6 mm diameter circular coupons. Blank control coupons containing no anti-biotic material were also molded. The coupons of each kind were placed on from two to six Petri dishes containing LB broth, each freshly inoculated with a culture of one of *Pseudomonas aeruginosa*, PAO1 Xen #41, or methicillin-resistant *Staphylococcus aureus* Xen #31 respectively. The cultures were incubated twenty-four hours at a temperature of 37° C. to allow the bacteria to grow. Measurements were made of the diameter of a circular zone of growth inhibition surrounding each coupon where no bacteria grew. The mean diameter, standard deviation and number of samples tested are presented in Table III below.

TABLE III

| | Zone of Inhibition | | | | | |
|---|---|---|---|---|---|---|
| | *P. aeruginosa*, | | | methicillin-resistant<br>*S. aureus* | | |
| | Mean,<br>mm | Std.<br>Dev. | n | Mean,<br>mm | Std.<br>Dev. | n |
| Blank Control,<br>18 wt. % VA/EVA | 0 | — | 3 | 0 | — | 3 |
| Blank Control,<br>32 wt. % VA/EVA | 0 | — | 3 | 0 | — | 3 |
| Example 1<br>Composite, 15 wt. %<br>ciprofloxacin<br>Weibull Dist.<br>18 wt. % VA/EVA | 25.1 | 1.7 | 6 | 0 | — | 3 |

TABLE III-continued

| | Zone of Inhibition | | | | | |
| | P. aeruginosa | | | methicillin-resistant S. aureus | | |
| | Mean, mm | Std. Dev. | n | Mean, mm | Std. Dev. | n |
|---|---|---|---|---|---|---|
| Example 2 Composite 3 wt. % ciprofloxacin Weibull Dist 18 wt. % VA/EVA | 19.2 | 1.5 | 6 | 0 | — | 6 |
| Example 3 Composite 6 wt. % ciprofloxacitn Weibull Dist 18 wt. % VA/EVA | 28.0 | 3.3 | 2 | 5.85 | 0.92 | 2 |
| Example 4 Composite 15 wt. % ciprofloxacin Log Normal Dist. 18 wt. % VA/EVA | 20.1 | 3.8 | 6 | 0 | — | 3 |
| Example 5 Composite 3 wt. % ciprofloxacin Log Normal Dist. 32 wt. % VA/EVA | 11.0 | 4.9 | 6 | 0 | — | 6 |
| Example 11 Composite 20 wt. % ciprofloxacin Weibull Dist. 60 wt. % EVA (32 wt. % VA/EVA), 20 wt. % PEG | 28.8 | 0.1 | 2 | 5.45 | 0.21 | 2 |

Example 14

The material prepared in Example 11 containing 20 wt. % ciprofloxacin was compression molded at a temperature of 175° C. into disks.

A cytotoxicity assay was run using fibroblasts derived from rabbit skin. Yellow MTT (3-(4,5-dimethylthiazol-2-yl)-2,5-diphenyltetrazolium bromide) was used to determine the cytotoxicity effect of the material of the invention. In this assay, MTT is reduced to purple formazan by metabolically active cells, and the purple formazan is measured by a spectrophotometer. This is widely accepted as a reliable way to examine cell proliferation which directly correlates with the level of cytotoxicity.

Fibroblasts grown to confluence in 100 cm plates were subcultured on 12-well plates and left undisturbed for 24 hours. After 24 hours, fibroblast cells were treated or untreated by the disks. The disks were incubated in the fibroblast for 24 hours followed by the addition of MTT and incubated for 3 hours at 37° C. After 3 hours, the resultant purple formazin was solubilized, incubated in the dark for 2 hours and quantified using a spectrophotometer at 595 nM.

No significant difference was seen between the absorbance values between treated and non-treated cellular populations. The results signify that cellular proliferation potential was not affected by the incubation of cells with the disks made from the material of the invention Example 15

A test was devised to assess the ability of a composite of the invention to kill bacteria in a surrounding fluid, and to prevent biofilm formation. The test, involving multiple challenges by an infectious biofilm forming bacteria, is regarded as very severe.

The composite prepared in Example 5 was compression molded into disks having a mass of 9.7±0.7 mg, approximating the mass of pediatric ear tubes. The disks contained 3 percent by weight of ciprofloxacin with a log normal particle size distribution uniformly dispersed in a 32 wt. % VA/EVA. Positive control disks consisting only of the same EVA, but no ciprofloxacin were also molded.

Bacteria inoculated nutrient medium was contained in the wells of a 96 well MBEC AssaySystem (BioSurface Technologies, Bozeman, Mont.) two plate assembly. The disks formed of the composite of the invention and also the control disks were fixed on polystyrene pegs attached to the top plate. Some parts of the top plate had no disks of either type attached as a negative control. Upon assembling the top plate onto the bottom plate each disk was immersed into one of the wells containing 100 µL of rich medium (brain heart Infusion broth) having $1\times10^5$ per mL of live bacteria ($1\times10^4$ bacteria per disk).

The species of bacteria used was Pseudomonas aeruginosa: a biofilm forming pathogen commonly found in ear tube infections (post-tympanostomy tube otorhea). A genetically bioluminescent strain, P. aeruginosa Xen 4, was used to assist in monitoring the growth of the bacteria in the medium surrounding the disk (plantonic growth) and on the disk itself (biofilm growth). The bacteria were incubated at 37° C., 5% $CO_2$ with 50 rpm orbital shaking.

After a 24 hour growth period, the top plate was removed from the assembly. The bottom plate containing the medium and plantonic bacteria was quantified for bioluminescence. The light emitted by the bacteria was measured using an IVIS™ Imaging System from Caliper Life Sciences, Hopkinton, Mass. Light emission was proportional to the quantity of active bacteria. Growth of bacteria in the fluid was also measured by the conventional method of optical density using a wavelength of 595 nM. Higher bacterial count causes more light to be blocked, and therefore higher optical density (ODs).

The top plate with the attached disks was rinsed in buffer to remove loosely adhered cells and placed in a new bottom plate containing fresh medium with another challenge of $1\times10^5$ CFU/ml bacteria freshly grown from an overnight culture. The MBEC plate was then quantified for a bioluminescence signal. Since the fresh inoculums consisted of too few bacteria to produce a detectable signal, and the previous planktonic bacteria had been removed, the only source of the signal was from biofilm bacteria attached to the disk and possibly to the polystyrene peg.

Measurements and re-Immersion in fresh medium was repeated five times per week.

Figure 9:
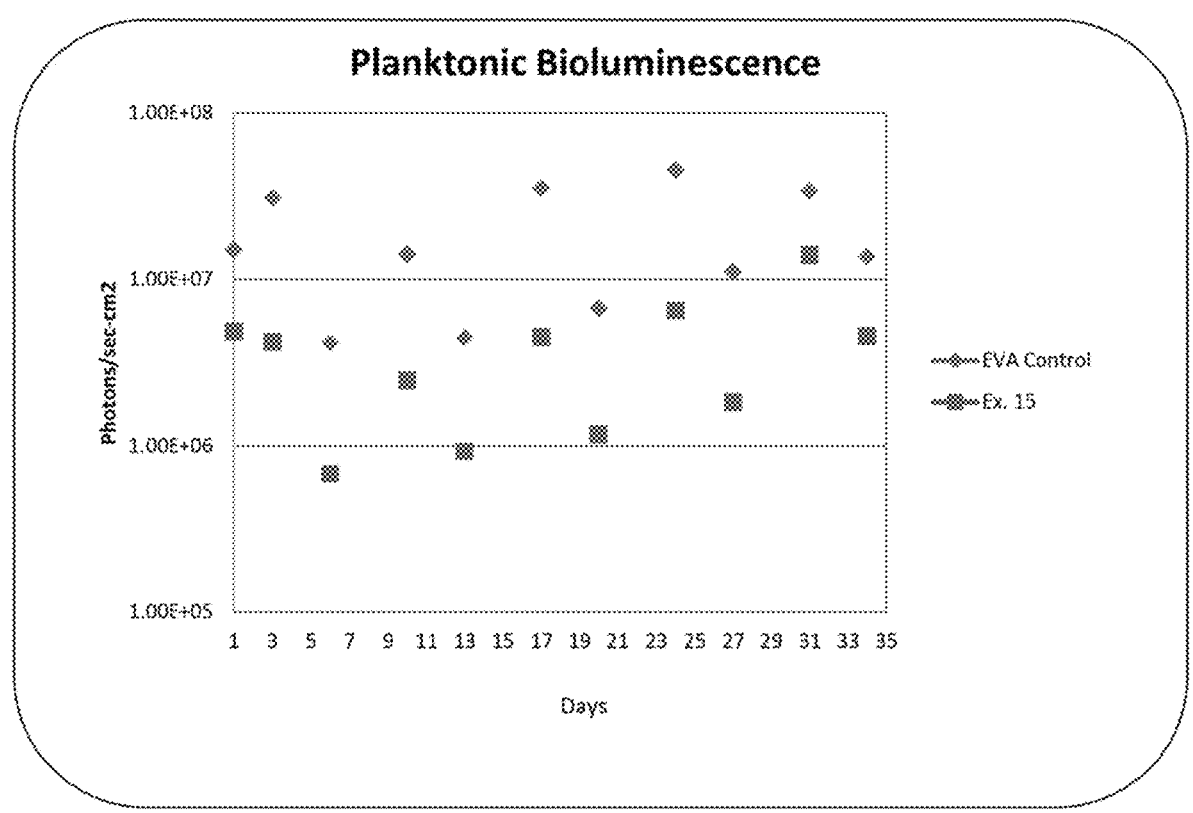
FIG. 9 is a plot of planktonic bioluminescence as a function of time for Example 15.

The measurements of bioluminescence of planktonic bacteria are presented in Table IV below and are plotted in FIG. 9. In FIG. 9, the squares are measurements for the wells that had disks formed of the composite of the Invention. The diamonds are measurements for wells containing the disks formed of the control EVA.

TABLE IV

Bioluminescence of Planktonic Bacteria in 100 µL
Avg Radiance
(photons/sec/cm2)
(mean values, n = 4 disks)

| Day | Control 32 wt. % VA/EVA | 3 wt. % ciprofloxacin, log normal distribution in 32 wt. % VA/EVA |
|---|---|---|
| 1 | 1.50E+07 | 4.88E+06 |
| 3 | 3.09E+07 | 4.22E+06 |
| 6 | 4.15E+06 | 6.76E+05 |
| 10 | 1.41E+07 | 2.47E+06 |
| 13 | 4.49E+06 | 9.26E+05 |
| 17 | 3.53E+07 | 4.52E+06 |
| 20 | 6.73E+06 | 1.18E+06 |
| 24 | 4.57E+07 | 6.54E+06 |
| 27 | 1.11E+07 | 1.83E+06 |
| 31 | 3.40E+07 | 1.40E+07 |
| 34 | 1.37E+07 | 4.59E+06 |
| 35 | 3.29E+07 | 2.25E+07 |

Figure 10:
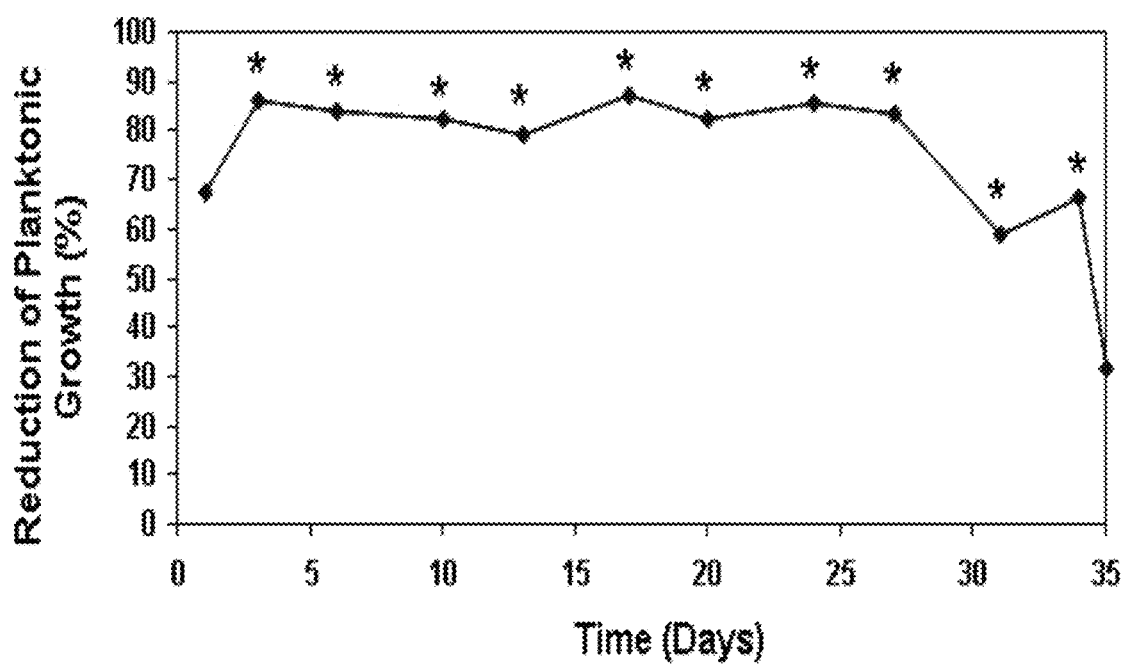
FIG. 10 is a plot of reduction in planktonic bacterial growth as measured by bioluminescence compared to the control as a function of time for Example 15.

The reduction of planktonic growth was determined from the bioluminescence measurements of the wells. Planktonic growth in the presence of disks formed of a composite of the invention is compared with that in the presence of control disks in FIG. 10. Statistically significant reductions as determined by a 2 tail t-test are indicated by "*". The disks formed of a composite of the invention caused a reduction in planktonic growth in the fluid of between 65 and 90% up to day 27. The reductions were statistically significant between days 2 and 34.

Figure 11:
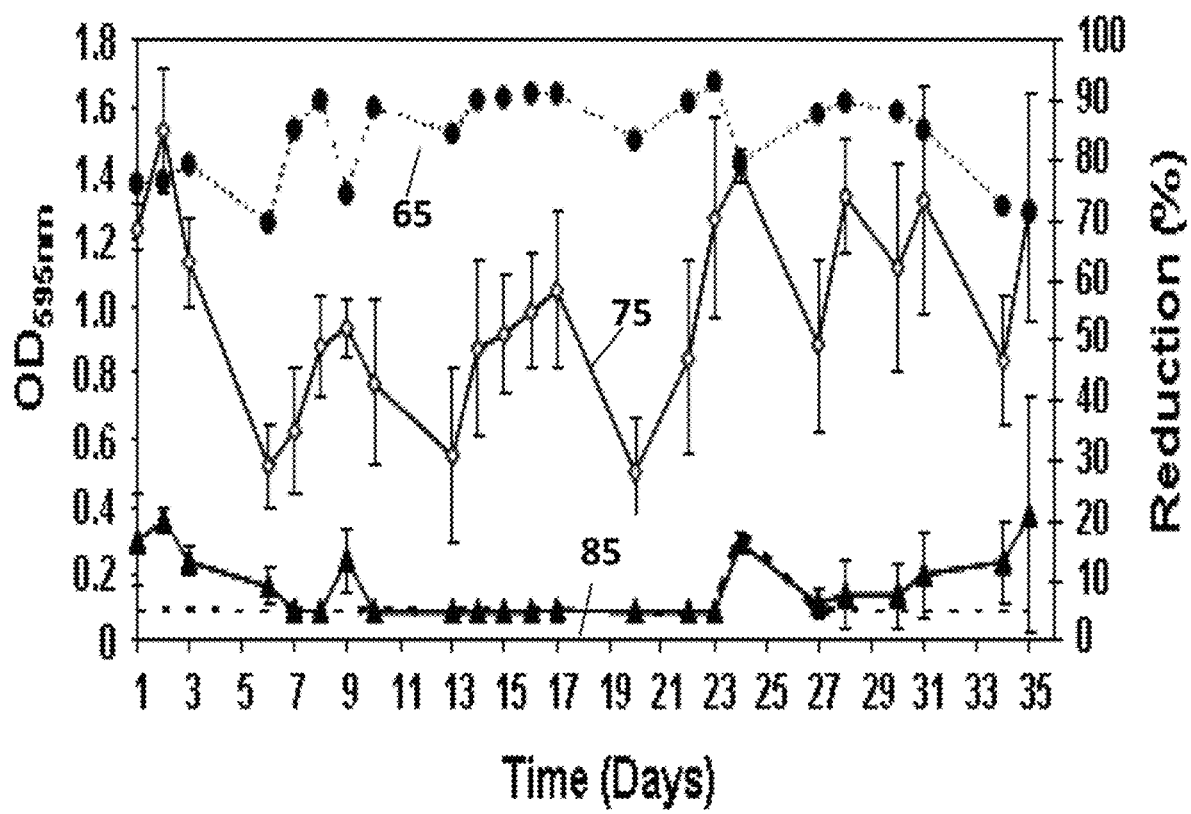
FIG. 11 is a plot of optical density and reduction in planktonic growth as measured by optical density compared to the control as a function of time for Example 15.

The measurements of optical density are presented in Table V below, and are plotted in FIG. 11.

TABLE V

Optical Density of Planktonic Bacteria in 100 µL
Optical Density (595 nm)

| | (−) control | | (+) Control 32 wt. % VA/EVA | | 3 wt. % ciprofloxacin, log normal distribution in 32 wt. % VA/EVA | |
|---|---|---|---|---|---|---|
| Day | mean | st dev | mean | st dev | mean | st dev |
| 1 | 0.186 | 0.108 | 1.235 | 0.390 | 0.298 | 0.039 |
| 2 | 0.139 | 0.060 | 1.528 | 0.195 | 0.362 | 0.035 |
| 3 | 0.136 | 0.069 | 1.136 | 0.253 | 0.236 | 0.041 |
| 6 | 0.186 | 0.174 | 0.525 | 0.205 | 0.160 | 0.056 |
| 7 | 0.729 | 0.582 | 0.631 | 0.160 | 0.095 | 0.005 |
| 8 | 0.545 | 0.454 | 0.881 | 0.273 | 0.088 | 0.004 |
| 9 | 0.637 | 0.475 | 0.935 | 0.254 | 0.241 | 0.099 |
| 10 | 0.490 | 0.399 | 0773 | 0.373 | 0.088 | 0.002 |
| 13 | 0.426 | 0.355 | 0.555 | 0.156 | 0.088 | 0.004 |
| 14 | 0.430 | 0.368 | 0.874 | 0.364 | 0.088 | 0.004 |
| 15 | 0.622 | 0.516 | 0.919 | 0.459 | 0.087 | 0.003 |
| 16 | 0.737 | 0.589 | 0.985 | 0.386 | 0.087 | 0.002 |
| 17 | 0.664 | 0.500 | 1.050 | 0.240 | 0.093 | 0.003 |
| 20 | 0.549 | 0.516 | 0.508 | 0.303 | 0.085 | 0.003 |
| 22 | 0.447 | 0.330 | 0.846 | 0.372 | 0.086 | 0.006 |
| 23 | 0.606 | 0.470 | 1.264 | 0.165 | 0.085 | 0.004 |
| 24 | 0.303 | 0.031 | 1.421 | 0.056 | 0.292 | 0.035 |
| 27 | 0.493 | 0.409 | 0.885 | 0.419 | 0.109 | 0.048 |
| 28 | 0.711 | 0.546 | 1.332 | 0.020 | 0.135 | 0.097 |
| 30 | 0.639 | 0.522 | 1.114 | 0.408 | 0.134 | 0.096 |
| 31 | 0.624 | 0.481 | 1.320 | 0.112 | 0.198 | 0.130 |
| 34 | 0.401 | 0.274 | 0.838 | 0.372 | 0.233 | 0.123 |
| 35 | 0.711 | 0.558 | 1.301 | 0.314 | 0.375 | 0.353 |

Optical density is a standard measure of the amount of bacterial growth in the fluid. In FIG. 11 line 85 represents measurements for the wells that had disks formed of the composite of the invention. Line 75 represents measurements for the wells that had disks formed of the EVA not containing ciprofloxacin. Error bars are 95% confidence limits calculated from data for 4 replicate disks.

The disks formed of the composite of the invention held planktonic growth at, or near zero in the fluid for the first 31 days. Planktonic growth was significantly less for wells containing a disk formed of the composite of the invention than for wells containing a disk formed of the control EVA. The percent reduction in optical density is shown in FIG. 11 as line 65 with reference to the right hand Y axis. The percent reduction in optical density ranged from 70 to 90%.

Figure 12:
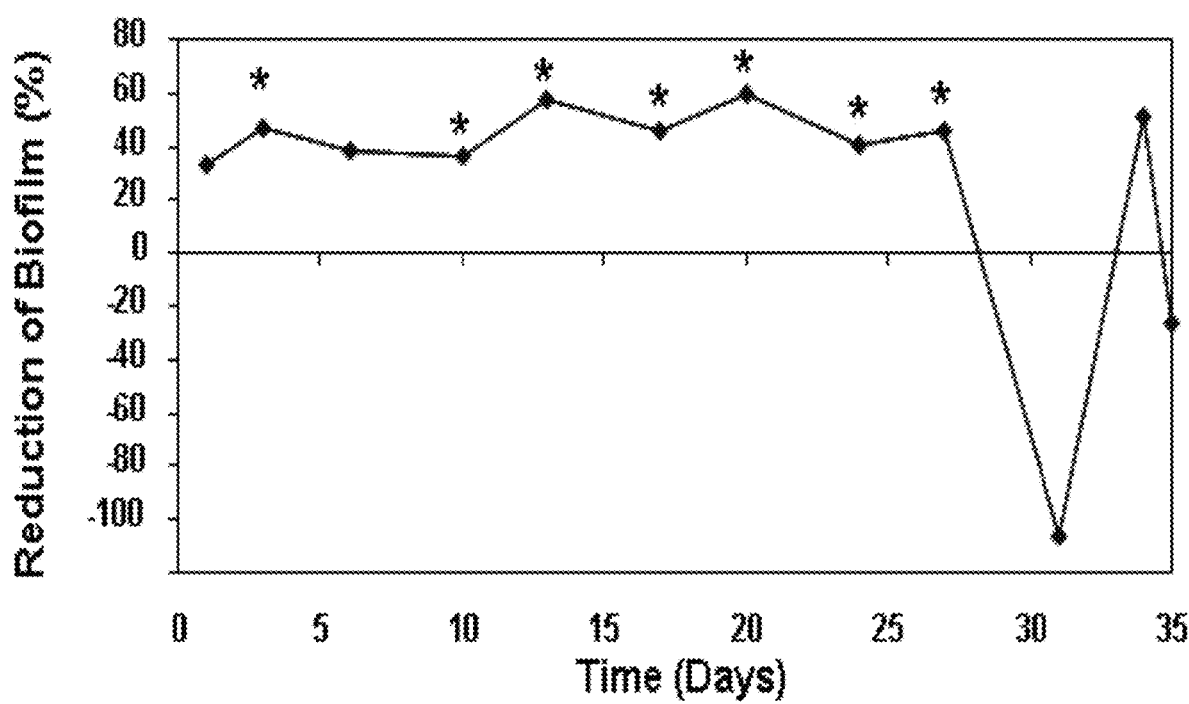
FIG. 12 is a plot of reduction in biofilm formation as a function of time for Example 15.

Percent reduction in biofilm formation on the disks formed from the composite of the invention compared to the control disks is shown in FIG. 12. Between days 2 and 27 the amount of the biofilm was reduced by approximately 50%. Statistically significant reductions as determined by the 2 tail t-test are indicated by the "*". At failure, the planktonic bacteria in the challenge medium survived and had formed biofilms on the surfaces of the depleted disks.

Example 16

In this example, the volume of medium was increased from 100 µL to 500 µL using a 48 well MBEC plate to more closely approximate the expected volume of effusion during an episode of chronic otitis media with infusion. Disks of the same weight as used in Example 15 consisting of composites of the invention, and also control disks containing no antibiotic, were placed directly into the 500 µL wells. The same concentration of *P. aeruginosa* Xen 4 was used so that the total challenge per disk was increased by a factor of 5 to $5 \times 10^4$ bacteria per disk. The medium in each well was replaced daily and optical density ($OD_{595}$) was measured.

The measurements of optical density are presented in Table VI below and are plotted in FIG. 13.

TABLE VI

Optical Density of Planktonic Bacteria in 500 µL

Figure 13:
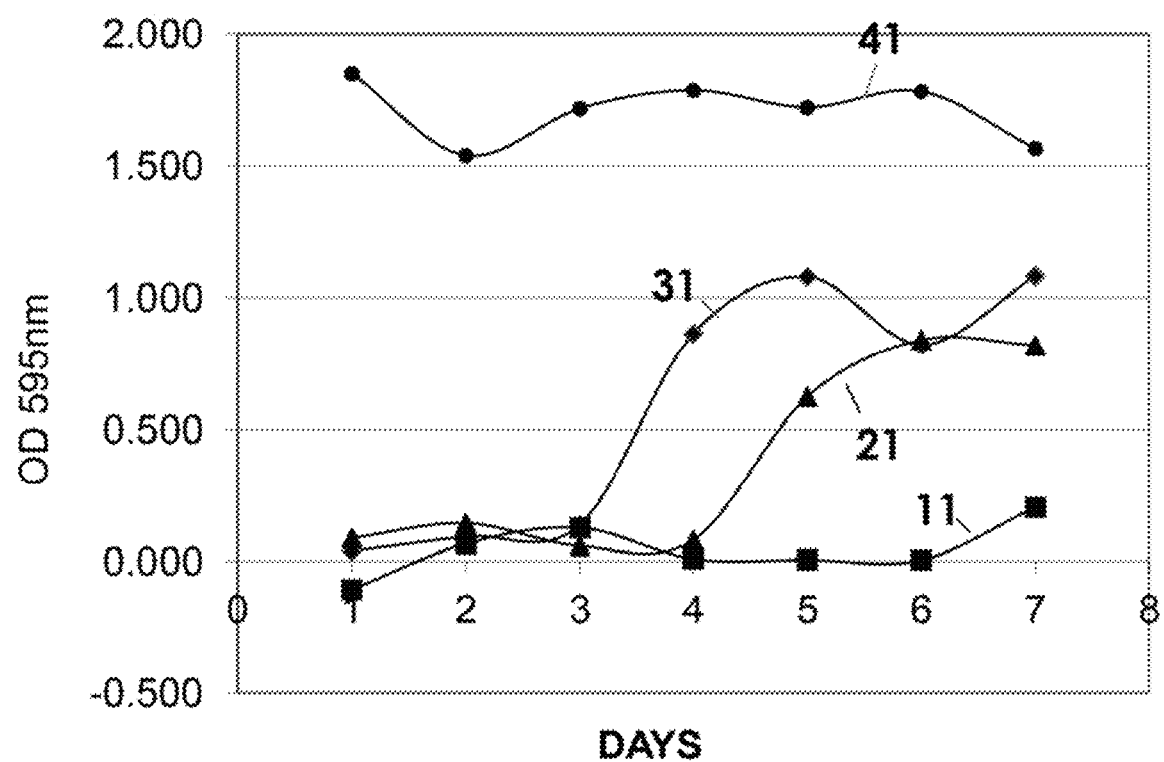
FIG. 13 is a plot of optical density as a function of time for Example 16.

| In FIG. 13 Day | Line 41 (+)Control 32 wt. % VA/EVA | Line 31 3 wt. % ciprofloxacin, log normal distribution in 32 wt. % VA/EVA | Line 21 3 wt. % ciproflaxacin, Weibull distribution in 18 wt. % VA/EVA | Line 11 20 wt. % ciprofloxacin Weibull Dist. 60 wt. % EVA(32 wt. % VA/EVA), 20 wt. % PEG |
|---|---|---|---|---|
| 1 | 1.850 | 0.039 | 0.089 | −0.107 |
| 2 | 1.540 | 0.094 | 0.145 | 0.067 |
| 3 | 1.718 | 0.139 | 0.058 | 0.127 |
| 4 | 1.786 | 0.865 | 0.081 | 0.009 |
| 5 | 1.721 | 1.079 | 0.625 | 0.006 |
| 6 | 1.782 | 0.823 | 0.841 | 0.005 |
| 7 | 1.566 | 1.082 | 0.821 | 0.205 |
| 8 | | | | In progress |

Example 17

1589 grams of an EVA containing 32 wt. % vinyl acetate designated ELVAX™ 150 were dry tumble mixed with 227 grams of polyethylene glycol (PEG) and 454 grams of ciprofloxacin. The mixture contained 20 wt. % ciprofloxacin, 10 wt % PEG and 70 wt. % EVA. The PEG from Sigma-Aldrich had a molecular weight of 8000 Daltons. The ciprofloxacin was from the same source as used in Example 1.

The mixture was fed at the rate of about 114 grams per minute into the feed throat of a 32 mm diameter co-rotating, fully intermeshing twin screw extruder having a 38:1 L/D. The temperature in the extruder was 38° C. at the inlet end and 132° C. thereafter. The screw speed was 250 RPM.

The polymer materials were melted, mixed and the ciprofloxacin was dispersed in the mixed polymer melt on passing through the extruder. Residence time in the extruder was approximately 2 minutes. The extrudate consisted of two strands, each approximately 5 mm in diameter. The strands were cooled in a water bath and chopped into pellets that were air dried.

At the conclusion of the above, when the extruder had run dry, the once-extruded pellets were fed back into the extruder under the same conditions as above and extruded and pelletized a second time. Microscopy of sections of the pellets showed uniform dispersion of the ciprofloxacin. Both the once-extruded and the twice-extruded materials were composite materials of the invention.

A control material was also prepared consisting of 20 wt. % PEG and 80 wt. % ELVAX™ 150 by the same procedure as described above.

Example 18

Coupons were compression molded from the twice-extruded composite material of the invention and the control material prepared in Example 17. Two healthy rabbits were intramuscularly implanted with four control coupons and four coupons consisting of the inventive composite material. One rabbit was sacrificed after 7 days and tissue biopsies were collected from all the implant sites, hematoxylin and eosin (H and E) stained, and inspected microscopically. The second rabbit was sacrificed after 30 days. The biopsies were evaluated for capsule formation and reaction. Neither the control nor the inventive materials caused intra-cutaneous irritation at either time point.

Example 19

Conventional, commercially available tympanostomy tubes (TTs) composed of fluoroplastic were obtained from Medtronic Xomed, Inc Jacksonville, Fla. (Model No. 1010171). The name of the product is Armstrong Modified Beveled Grommet Ventilation tube. The TTs had an inner diameter of 1.14 mm and an inner flange diameter of 3.5 mm.

An injection molding die was fabricated to duplicate the dimensions of the conventional TTs. The twice-extruded material of the invention prepared in Example 17 was then injection molded to prepare tympanostomy tubes of the invention having the same dimensions as the commercial TTs described above. To test the ability of the inventive TTs to prevent infection via transmission from the ear canal, the *Chinchilla laniger* animal model was used. Tubes were place in either the left, or right, or both ears of an anesthetized *Chinchilla*. Eight animals received the commercially available control TTs (three right ear only, two left ear only, and three both ears). Eleven animals received the inventive TTs (three right ear only, four left ear only, and four both ears), The animals were left for a minimum of 10 days for the tympanic membrane to heal, which was confirmed by otoscopic examination.

One cohort of animals with 2 control and 4 inventive TTs was inoculated on Apr. 12, 2011 and the second cohort was inoculated on Apr. 25, 2011. Inoculation was achieved by gently syringe dropping 500 µL of *P. aeruginosa* PAO1 into the ear canal of each ear containing a TT. Seven of the animals with control TTs either died overnight (2 animals) or were euthanized (5 animals) to reduce suffering within 5 days post inoculation. The decision to euthanize was made by the animal husbandry personnel who were binded to the type of TT placed. The remaining control animal was euthanized 18 days post inoculation. It was noted that the tube was out of place.

In the animals with inventive TTs, two animals died within 4 days of inoculation. One of these had no sign of infection, and in the other, it was noted that a tube was out of place. A third was euthanized 18 days post inoculation and it was noted that the TT had come out of position. The remaining 8 animals remained healthy and were re-inoculated with a high concentration of *P. aeruginosa* on May $9^{th}$. No animals showed signs of infection and they were re-inoculated with a third and fourth challenge on May $16^{th}$ and May 23.

Figure 14:
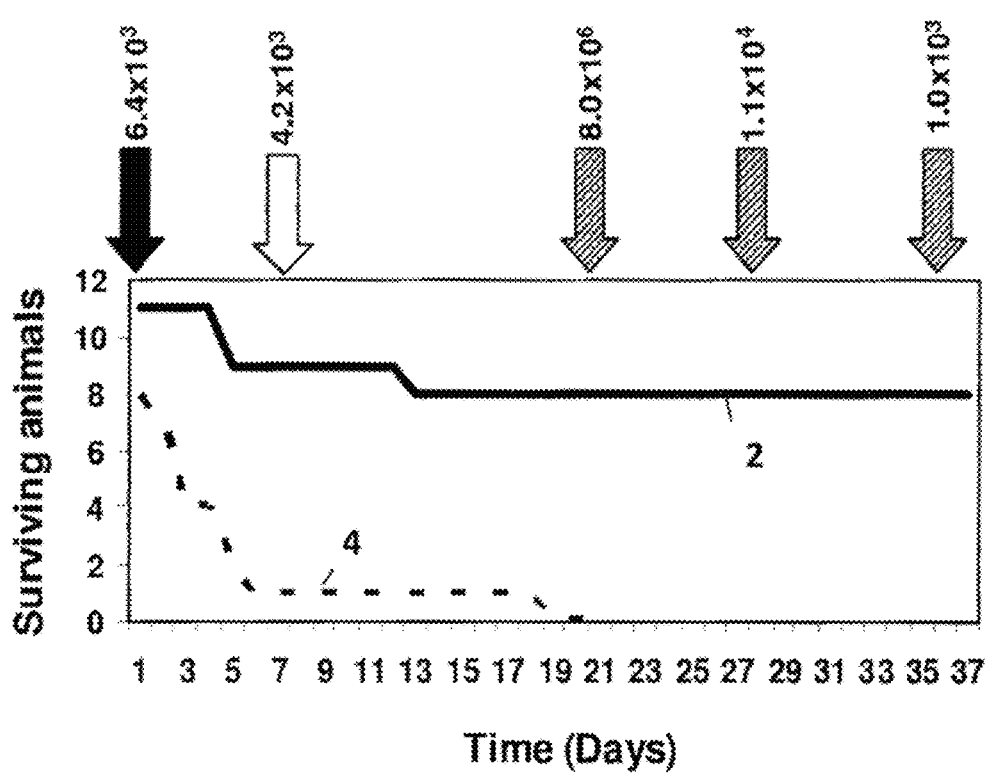
FIG. 14 is a plot of *Chinchilla* survival as a function of time after ear canal challenge in Example 19.

FIG. 14 shows the survival time of Chinchillas containing control (line 4) or inventive TTs (line 2). The arrows are place at the times of inoculation and the numerals above the arrows show the number of inoculated bacteria (as CFU) per ear. One cohort of animals was inoculated at day 0 (black arrow) and the second cohort was inoculated on day 7 (white arrow). Subsequent re-inoculations are shown by hashed arrows.

In summary, none of the 8 animals with the control tubes survived longer than 18 days after receiving one Inoculation. This contrasted with animals with inventive TTs in which 8 survived 36 days and 4 different inoculations up to the time of writing. Of the three animals that died, two had rejected the ear tubes. These data demonstrate that the inventive tubes provide a high level of prophylactic protection against infection when challenged via the ear canal with the pathogenic bacteria *P. aeruginosa* PAO1. Tissue biopsies of an animal with inventive ear tubes sacrificed after 35 days showed no irritation.

Figure 15:
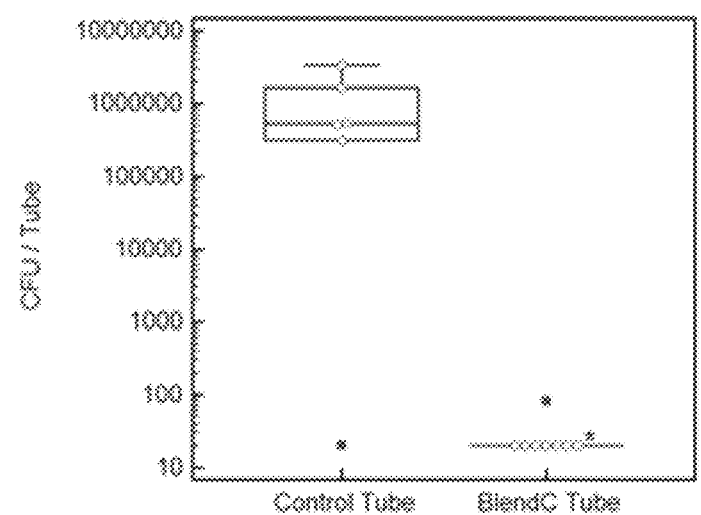
FIG. 15 is a plot showing the bacterial count on the tympanostomy tubes after ear canal challenge and removal from the animals in Example 19.

Both the control and inventive TTs removed from the animals were examined and the number of bacteria adhering to the TTs were measured. The data are shown in FIG. 15. The inventive TTs are designated "Blend C Tube". It will be seen that the bacterial colonization of the inventive TTs was about four orders of magnitude lower than the control TTs.

Example 20

Figure 16:
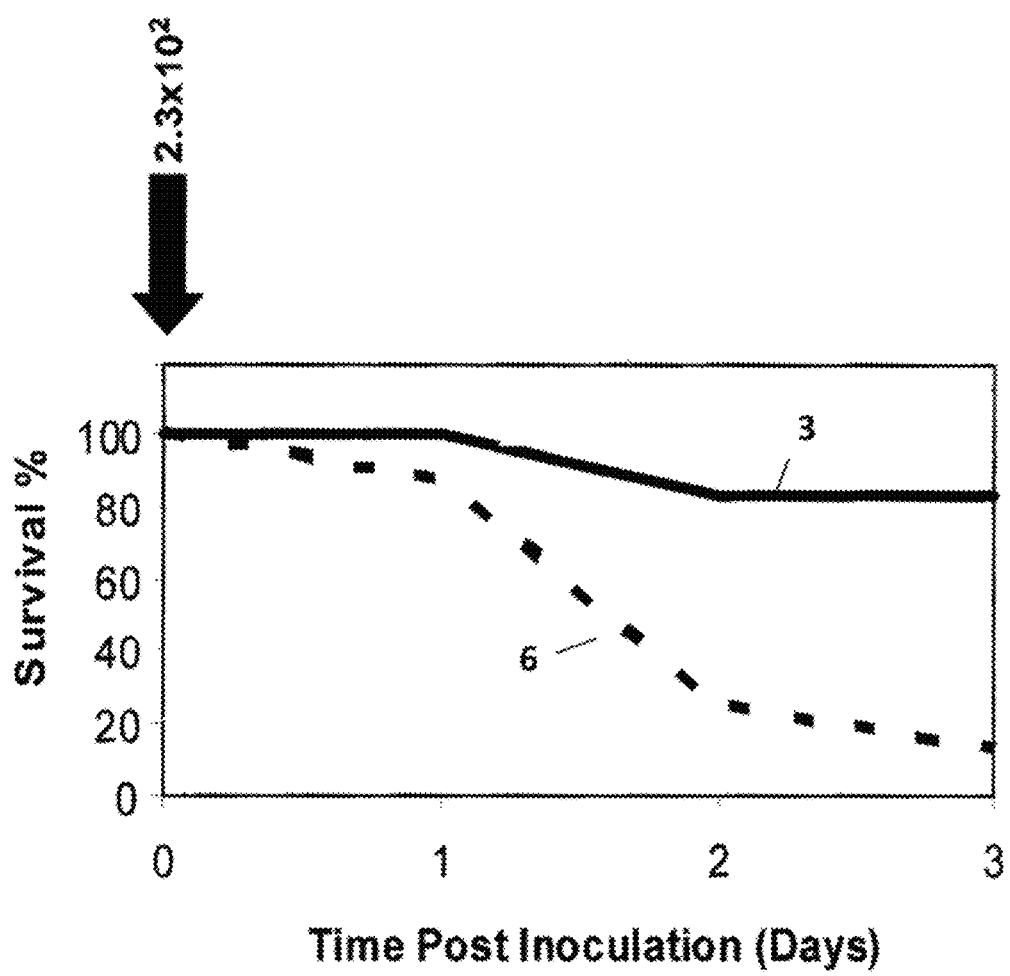
FIG. 16 is a plot of *Chinchilla* survival percent after transbullar challenge in Example 20.

Eight Chinchillas had the control TTs and six had the inventive TTs inserted. After a period of 10 or 11 days to allow the incisions to heal, and the animals were confirmed to be healthy, they were inoculated with 230 CFU *P. aeruginosa* PAO1 Xen41 directly into the middle ear using the transbullar approach. The survival curve (FIG. 16) showed that the animals with the inventive TTs (line 3) had a longer survival time than those with the control tubes (line 6), demonstrating that the inventive tubes were more effective in preventing otis media than the control tubes.

Example 21

The transbullar challenge was repeated with new animals and fresh TTs prepared as in Example 19. The animals were inoculated with *H. Influenzae* Pitt II directly into the middle ear using the transbullar approach. None of the animals died as a result of infection.

Figure 17:
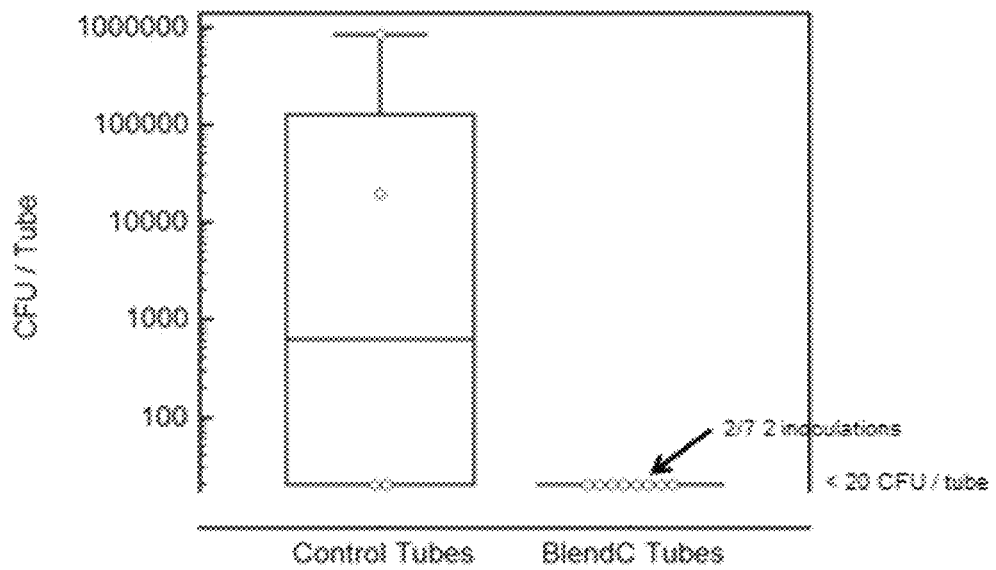
FIG. 17 is a plot showing the bacterial count on the tympanostomy tubes after transbullar challenge and removal from the animals in Example 21.

Both the control and inventive TTs removed from the animals were examined and the number of bacteria adhering to the TTs were measured. The data are shown in FIG. 17. The inventive TTs are designated "Blend C Tube". It will be seen that the bacterial colonization of the inventive TTs was at least two orders of magnitude lower than the control TTs.

Example 22

Eleven Chinchillas received transbullar Inoculation (without ear tubes placed in the ear drum) with *H. Influenzae* Pitt II ("H. Flu") at 1.7×10E2 cfu/ear in 100 μL bolus to establish robust Infection in the middle ear. Control ear tubes were placed in five of the eleven Chinchillas 4 days after the transbullar inoculation with the H. Flu. The remaining six Chinchillas received the inventive ear tubes at same time 4 days after the transbullar inoculation.

Both control and inventive tubes removed from the animals after one week were sonicated and the number of bacteria adhering to the TTs was measured by a culture method. It is demonstrated in FIG. 18 that the bacterial colonization of the inventive tubes was at least 3 orders of magnitude lower than on the control tubes. In FIG. 18, the inventive TTs are designated "Blend C Tube".

Further speciation of the recovered bacteria from the control tubes with Polymerase Chain Reaction (PCR) showed that the H. Flu is the main bacterial specie present on the tubes and has the same genetic signature as the organism used in the inoculum. When the organisms recovered from the inventive tubes were analyzed by PCR there was no evidence of the H. Flu found. The few organisms found on the inventive tube were similar to those present in healthy Chinchillas.

The results of this example demonstrate that placing the inventive ear tube in the ear drum is able to treat an established infection in the middle ear. These results are also significant since there is always an established middle ear Infection present before myringotomy. Since otitis media infection normally exists in the form of biofilm, the results of this example support that placement of the inventive ear tube can eradicate biofilm present on middle ear mucosa. Accordingly, the inventive tube may eliminate the need for administering topical antibiotic otic drops such as Ciprodex® or oral systemic antibiotics after myringotomy.

Having thus described the invention in rather full detail, it will be understood that such detail need not be strictly adhered to but that further changes and modifications may suggest themselves to one skilled in the art, all falling within the scope of the invention as defined by the subjoined claims.

What is claimed is:

1. A method of treatment, said method comprising introducing a tympanostomy tube into a tympanic membrane, said tympanostomy tube formed from a molded composite comprising:
    a) a melt blend of:
        (i) an ethylene-vinyl acetate copolymer having a melt index less than 50 g/10 min. as measured by ASTM D1238 and comprising 10 to 50 percent by weight of vinyl acetate,
        (ii) polyethylene glycol having a weight average molecular weight of from about 2,000 to about 20,000 Daltons; and
    b) about 1 to about 30 percent by weight ciprofloxacin betaine dispersed throughout said melt blend forming said molded composite; said molded composite comprising:
        i) a first phase with said melt blend comprised of from about 0.1 to about 30 percent by weight of said ciprofloxacin betaine; and
        ii) a second phase with said melt blend comprised of from about 95 to about 99.99 percent by weight of said ciprofloxacin betaine; and
        iii) a third phase comprising undissolved ciprofloxacin betaine; and
    wherein said molded composite provides a release of said ciprofloxacin betaine to a surrounding fluid over a time period of at least 30 days.

2. The method of claim 1, wherein said ciprofloxacin betaine before dispersion in said melt blend has a cumulative particle size distribution described by the following Weibull distribution:

$$F = 1 - e^{-\left(\frac{d}{D}\right)^S};$$

where:
d is the particle size, microns;
e is the base of natural logarithms equal to 2.71828 approximately;
F is the cumulative size fraction of particles smaller than d;
D is a characteristic size for the distribution, microns;
S is a shape factor for the distribution;
said distribution having a characteristic size of from about 5 to about 100 micrometers and a shape factor from about 1.1 to about 5, with an index of determination upon regression of at least about 0.90;
said index of determination being higher than obtained by regression of particle size against any of: a normal distribution, a log normal distribution, an exponential distribution, or an extreme value distribution.

3. The method of claim 1 or 2 wherein said composite comprises one or more bioactive agents additional to the ciprofloxacin betaine selected from the group consisting of carbapenems, cephalosporins, penicillins, lincosamides, tetracyclines, macrolides, glycopeptides, quinolones, oxazolidinones, aminoglycosides, gyrase inhibitors, and their combination.

4. The method of claim 1, wherein said composite further comprises a bioactive anti-inflammatory agent.

5. The method of claim 3, wherein a compression molded disk of said composite when placed in contact with a brain heart infusion broth having $1\times10^5$ per mL of bioluminescent *Pseudomonas aeruginosa* Xen 4 and incubated at 37° C., 5% $CO_2$ with 50 rpm orbital shaking, after rinsing to remove loosely adhered cells, shows less adhered biofilm than a control disk not containing ciprofloxacin but of otherwise the same composition and identically treated.

6. The method of claim 3, wherein said one or more bioactive agents additional to the ciprofloxacin betaine is selected from the group consisting of meropenem, ceftazidime, amoxicillin, clindamycin, tetracycline, erythromycin, vancomycin, ciprofloxacin hydrochloride, linezolid, usnic acid, sodium usnate, polyhexamethylene biguanide, and their combination.

7. The method of claim 1, wherein said ciprofloxacin betaine and said melt blend are subjected to a temperature sufficient to keep the melt blend as a melt and shear for at least about 1 minute to form the phases.

8. The method of claim 1, wherein the molded composite comprises about 1 to about 25 percent by weight of the ciprofloxacin betaine.

9. A method of reducing biofilm formation, said method comprising introducing a tympanostomy tube into a tympanic membrane, said tympanostomy tube formed from a molded composite comprising:
   a) a melt blend of:
      (i) an ethylene-vinyl acetate copolymer having a melt index less than 50 g/10 min. as measured by ASTM D1238 and comprising 10 to 50 percent by weight of vinyl acetate,
      (ii) polyethylene glycol having a weight average molecular weight of from about 2,000 to about 20,000 Daltons; and
   b) about 1 to about 30 percent by weight ciprofloxacin betaine dispersed throughout said melt blend forming said molded composite; said molded composite comprising:
      i) a first phase with said melt blend comprised of from about 0.1 to about 30 percent by weight of said ciprofloxacin betaine; and
      ii) a second phase with said melt blend comprised of from about 95 to about 99.99 percent by weight of said ciprofloxacin betaine; and
      iii) a third phase comprising undissolved ciprofloxacin betaine; and
   wherein said molded composite provides a release of said ciprofloxacin betaine to a surrounding fluid over a time period of at least 30 days.

10. The method of reducing biofilm formation as in claim 9, wherein said ciprofloxacin betaine before dispersion in said melt blend has a cumulative particle size distribution described by the following Weibull distribution $$F = 1 - e^{-\left(\frac{d}{D}\right)^{S}};$$

where:
d is the particle size, microns;
e is the base of natural logarithms equal to 2.71828 approximately;
F is the cumulative size fraction of particles smaller than d;
D is a characteristic size for the distribution, microns;
S is a shape factor for the distribution;
said distribution having a characteristic size of from about 5 to about 100 micrometers and a shape factor from about 1.1 to about 5, with an index of determination upon regression of at least about 0.90;
said index of determination being higher than obtained by regression of particle size against any of: a normal distribution, a log normal distribution, an exponential distribution, or an extreme value distribution.

11. The method of reducing biofilm formation as in claim 9 or 10 wherein said composite comprises one or more bioactive antibiotics additional to the ciprofloxacin betaine selected from the group consisting of carbapenems, cephalosporins, penicillins, lincosamides, tetracyclines, macrolides, glycopeptides, quinolones, oxazolidinones, aminoglycosides, gyrase inhibitors, and their combination.

12. The method of reducing biofilm formation as in claim 9 or 10, wherein a compression molded disk of said composite when placed in contact with a brain heart infusion broth having $1 \times 10^5$ per mL of bioluminescent *Pseudomonas aeruginosa* Xen 4 and incubated at 37° C., 5% $CO_2$ with 50 rpm orbital shaking for periods of 1 to 35 days, after rinsing to remove loosely adhered cells, shows less adhered biofilm than a control disk not containing ciprofloxacin but of otherwise the same composition and identically treated.

13. The method of reducing biofilm formation as in claim 9 or 10, wherein said composite includes a bioactive anti-inflammatory agent.

14. The method of reducing biofilm formation as described in claim 11, wherein said one or more bioactive antibiotics additional to the ciprofloxacin betaine is selected from the group consisting of beta lactam, meropenem, ceftazidime, amoxicillin, clindamycin, tetracycline, erythromycin, vancomycin, ciprofloxacin hydrochloride, linezolid, usnic acid, sodium usnate, polyhexamethylene biguanide, and their combination.

15. The method of reducing biofilm formation as in claim 9, wherein said ciprofloxacin betaine and said melt blend are subjected to a temperature sufficient to keep the melt blend as a melt and shear for at least about 1 minute to form the phases.

16. The method of reducing biofilm formation as in claim 9, wherein the molded composite comprises about 1 to about 25 percent by weight of the ciprofloxacin betaine.

* * * * *